(12) United States Patent
Nothacker et al.

(10) Patent No.: US 10,631,767 B2
(45) Date of Patent: Apr. 28, 2020

(54) WEARABLE SYSTEM AND METHOD FOR MONITORING INTOXICATION

(71) Applicant: KHN Solutions, Inc., San Francisco, CA (US)

(72) Inventors: Keith Harry Nothacker, San Francisco, CA (US); Will Tammen, San Francisco, CA (US); Imraan Aziz, San Francisco, CA (US)

(73) Assignee: KHN Solutions, Inc., San Francisco, CA (US)

( * ) Notice: Subject to any disclaimer, the term of this patent is extended or adjusted under 35 U.S.C. 154(b) by 0 days.

(21) Appl. No.: 16/218,357

(22) Filed: Dec. 12, 2018

(65) Prior Publication Data

US 2019/0110721 A1 Apr. 18, 2019

Related U.S. Application Data

(63) Continuation of application No. 15/666,062, filed on Aug. 1, 2017, now Pat. No. 10,182,752, which is a
(Continued)

(51) Int. Cl.
*A61B 5/1477* (2006.01)
*G01N 27/416* (2006.01)
(Continued)

(52) U.S. Cl.
CPC ............ *A61B 5/1477* (2013.01); *A61B 5/082* (2013.01); *A61B 5/14546* (2013.01); *A61B 5/18* (2013.01);
(Continued)

(58) Field of Classification Search
CPC ... A61B 5/1477; A61B 5/082; A61B 5/14546; A61B 5/18; A61B 5/4023; A61B 5/4845; A61B 5/4863; A61B 5/681; A61B 5/7275; A61B 10/0064; G01N 27/416; G01N 33/4972; G06F 19/00
(Continued)

(56) References Cited

U.S. PATENT DOCUMENTS 4,487,055 A 12/1984 Wolf
4,749,553 A 6/1988 Lopez et al.
(Continued)

FOREIGN PATENT DOCUMENTS

FR 2975522 A1 11/2012

OTHER PUBLICATIONS

STIC Search Results. 15205876-528781-Search Results.pdf.

*Primary Examiner* — Kerri L McNally
(74) *Attorney, Agent, or Firm* — Jeffrey Schox; Caitlin Ploch

(57) ABSTRACT

A system for transdermal alcohol sensing to be worn near a skin surface of a user, including: an alcohol sensor; a microporous membrane; a housing coupled to the alcohol sensor and the membrane, defining a volume between the alcohol sensor and a first membrane side, and fluidly isolating the volume from a second membrane side opposing the first membrane side; an electronics subsystem electrically coupled to the alcohol sensor, operable to power and receive signals from the alcohol sensor; and a fastener operable to position the second membrane side proximal the skin surface.

18 Claims, 33 Drawing Sheets

Related U.S. Application Data continuation of application No. 15/375,801, filed on Dec. 12, 2016, now Pat. No. 9,788,772, which is a continuation-in-part of application No. 15/294,317, filed on Oct. 14, 2016, now Pat. No. 9,872,649, which is a continuation of application No. 14/925,675, filed on Oct. 28, 2015, now Pat. No. 9,662,065, which is a continuation of application No. 14/631,125, filed on Feb. 25, 2015, now Pat. No. 9,192,334, which is a continuation-in-part of application No. 14/470,376, filed on Aug. 27, 2014, now Pat. No. 9,076,317, which is a continuation of application No. 14/169,029, filed on Jan. 30, 2014, now Pat. No. 8,878,669.

(60) Provisional application No. 61/812,704, filed on Apr. 16, 2013, provisional application No. 61/759,390, filed on Jan. 31, 2013, provisional application No. 62/269,854, filed on Dec. 18, 2015.

(51) Int. Cl.

| | | |
|---|---|---|
| *A61B 5/145* | (2006.01) | |
| *A61B 5/00* | (2006.01) | |
| *A61B 10/00* | (2006.01) | |
| *A61B 5/08* | (2006.01) | |
| *A61B 5/18* | (2006.01) | |
| *G01N 33/497* | (2006.01) | |
| *G06F 19/00* | (2018.01) | |
| *A61B 5/097* | (2006.01) | |

(52) U.S. Cl.
CPC .......... *A61B 5/4023* (2013.01); *A61B 5/4845* (2013.01); *A61B 5/4863* (2013.01); *A61B 5/681* (2013.01); *A61B 5/7275* (2013.01); *A61B 10/0064* (2013.01); *G01N 27/416* (2013.01); *G01N 33/4972* (2013.01); *G06F 19/00* (2013.01); *A61B 5/0022* (2013.01); *A61B 5/097* (2013.01); *A61B 5/486* (2013.01); *A61B 5/7282* (2013.01); *A61B 2010/0009* (2013.01); *A61B 2503/22* (2013.01); *A61B 2562/0219* (2013.01)

(58) Field of Classification Search
USPC ........................................................ 340/576
See application file for complete search history.

(56) References Cited

U.S. PATENT DOCUMENTS

| | | |
|---|---|---|
| 4,996,161 A | 2/1991 | Conners et al. |
| D333,441 S | 2/1993 | Greene |
| 5,216,415 A | 6/1993 | Ono et al. |
| 5,220,919 A | 6/1993 | Phillips et al. |
| 5,291,898 A | 3/1994 | Wolf |
| 5,426,415 A | 6/1995 | Prachar et al. |
| D362,642 S | 9/1995 | Howse |
| D381,885 S | 8/1997 | Lane |
| 5,944,661 A * | 8/1999 | Swette ............... A61B 10/0064 204/403.06 |
| 6,026,674 A | 2/2000 | Gammenthaler |
| 6,075,444 A | 6/2000 | Sohege et al. |
| 6,433,863 B1 | 8/2002 | Weiss |
| 6,454,723 B1 | 9/2002 | Montagnino |
| 6,556,905 B1 | 4/2003 | Mittelsteadt et al. |
| 6,608,399 B2 | 8/2003 | McConnell et al. |
| 6,726,636 B2 | 4/2004 | Der et al. |
| 6,824,520 B2 | 11/2004 | Orr et al. |
| 6,853,956 B2 | 2/2005 | Ballard et al. |
| 6,858,182 B1 | 2/2005 | Ito et al. |
| 6,899,683 B2 | 5/2005 | Mault et al. |
| 6,956,484 B2 | 10/2005 | Crespo |
| D521,885 S | 5/2006 | Eddy et al. |
| D530,424 S | 10/2006 | Manser et al. |
| D539,683 S | 4/2007 | Shaw et al. |
| D539,684 S | 4/2007 | Kitamura et al. |
| 7,204,335 B2 | 4/2007 | Stewart et al. |
| 7,256,700 B1 | 8/2007 | Ruocco et al. |
| 7,311,665 B2 | 12/2007 | Hawthorne et al. |
| 7,341,693 B2 | 3/2008 | Der et al. |
| 7,462,149 B2 | 12/2008 | Hawthorne et al. |
| D586,677 S | 2/2009 | Nothacker et al. |
| D603,281 S | 11/2009 | Gonzalez |
| 7,611,461 B2 | 11/2009 | Hawthorne et al. |
| D606,434 S | 12/2009 | Castrodale et al. |
| 7,641,611 B2 | 1/2010 | Hawthorne et al. |
| 7,823,681 B2 | 11/2010 | Crespo et al. |
| 7,930,927 B2 | 4/2011 | Cooper et al. |
| 7,934,577 B2 | 5/2011 | Walter et al. |
| 8,040,233 B2 | 10/2011 | Adappa et al. |
| 8,078,334 B2 | 12/2011 | Goodrich |
| 8,126,735 B2 | 2/2012 | Dicks et al. |
| 8,165,824 B2 | 4/2012 | Iiams et al. |
| 8,240,419 B2 | 8/2012 | Zimmermann et al. |
| 8,258,968 B2 | 9/2012 | Ghazarian et al. |
| 8,280,436 B2 | 10/2012 | Harris |
| 8,317,697 B2 | 11/2012 | Hawthorne et al. |
| 8,370,027 B2 | 2/2013 | Pettersson et al. |
| 8,381,573 B2 | 2/2013 | Keays |
| 8,453,492 B2 | 6/2013 | Tsuzuki et al. |
| 8,466,796 B1 | 6/2013 | Mejia et al. |
| 8,505,360 B2 | 8/2013 | Ruocco et al. |
| 8,657,744 B2 | 2/2014 | Rompa et al. |
| 8,693,597 B2 | 4/2014 | Sexton et al. |
| 8,707,758 B2 | 4/2014 | Keays |
| D705,100 S | 5/2014 | Nothacker et al. |
| 8,808,228 B2 | 8/2014 | Brister et al. |
| 8,814,804 B2 | 8/2014 | Walden et al. |
| 8,849,387 B2 | 9/2014 | Gilbert et al. |
| 8,862,152 B1 | 10/2014 | Buchholz et al. |
| 8,878,669 B2 | 11/2014 | Nothacker et al. |
| 8,920,725 B2 | 12/2014 | Withrow et al. |
| 8,941,501 B1 | 1/2015 | Debijl |
| 8,957,771 B2 | 2/2015 | Arringdale et al. |
| D724,980 S | 3/2015 | Nothacker et al. |
| D727,763 S | 4/2015 | Nothacker et al. |
| D727,764 S | 4/2015 | Nothacker et al. |
| 9,020,773 B2 | 4/2015 | Son et al. |
| D731,341 S | 6/2015 | Kobayakawa |
| 9,045,101 B2 | 6/2015 | Phelan |
| 9,063,120 B2 | 6/2015 | Park |
| 9,076,317 B2 | 7/2015 | Nothacker et al. |
| 9,095,251 B2 | 8/2015 | Purks et al. |
| 9,192,324 B2 | 11/2015 | Phillips et al. |
| 9,192,334 B2 | 11/2015 | Nothacker et al. |
| 9,228,997 B2 | 1/2016 | Keays |
| 9,239,323 B2 | 1/2016 | Keays |
| 9,241,659 B2 | 1/2016 | Rompa et al. |
| 9,241,661 B2 | 1/2016 | Shnaper et al. |
| 9,278,696 B2 | 3/2016 | Yi et al. |
| 9,398,858 B2 | 7/2016 | Phillips et al. |
| 9,417,232 B2 | 8/2016 | Keays et al. |
| 9,442,103 B1 | 9/2016 | Goad |
| 9,481,245 B2 | 11/2016 | Nelson |
| 9,489,487 B2 | 11/2016 | Hawthorne et al. |
| 9,662,065 B2 | 5/2017 | Nothacker et al. |
| 9,746,456 B2 | 8/2017 | Keays |
| 9,788,772 B2 * | 10/2017 | Nothacker .............. G06F 19/00 |
| 9,829,480 B2 | 11/2017 | Wojcik et al. |
| 9,855,000 B2 | 1/2018 | Lansdorp et al. |
| 9,881,997 B2 | 1/2018 | Sakata et al. |
| 9,922,508 B2 | 3/2018 | Keays et al. |
| 10,040,349 B2 | 8/2018 | Devries et al. |
| 10,182,752 B2 * | 1/2019 | Nothacker .............. G06F 19/00 |
| 2002/0008966 A1 | 1/2002 | Fjelstad et al. |
| 2002/0084130 A1 | 7/2002 | Der et al. |
| 2002/0128769 A1 | 9/2002 | Der et al. |
| 2002/0140289 A1 | 10/2002 | McConnell et al. |
| 2002/0143267 A1 | 10/2002 | Montagnino |
| 2003/0116159 A1 | 6/2003 | Orr et al. |
| 2003/0117287 A1 | 6/2003 | Crespo |
| 2003/0176803 A1 | 9/2003 | Gollar |

(56) References Cited

U.S. PATENT DOCUMENTS

| | | | |
|---|---|---|---|
| 2005/0241871 A1 | 11/2005 | Stewart et al. | |
| 2006/0193749 A1 | 8/2006 | Ghazarian et al. | |
| 2006/0217624 A1 | 9/2006 | Myklebust et al. | |
| 2006/0217625 A1 | 9/2006 | Forrester | |
| 2006/0282344 A1 | 12/2006 | Brown | |
| 2006/0293613 A1 | 12/2006 | Fatehi et al. | |
| 2007/0024454 A1 | 2/2007 | Singhal | |
| 2007/0093725 A1 | 4/2007 | Shaw | |
| 2007/0144812 A1 | 6/2007 | Stewart et al. | |
| 2007/0296601 A1 | 12/2007 | Sultan et al. | |
| 2008/0045806 A1* | 2/2008 | Keppler | A61B 5/0002 600/300 |
| 2008/0097793 A1 | 4/2008 | Dicks et al. | |
| 2008/0183388 A1 | 7/2008 | Goodrich | |
| 2008/0262469 A1 | 10/2008 | Brister et al. | |
| 2009/0043409 A1 | 2/2009 | Ota | |
| 2009/0090577 A1 | 4/2009 | Takahashi et al. | |
| 2009/0182216 A1 | 7/2009 | Roushey et al. | |
| 2009/0201138 A1 | 8/2009 | Ghazarian et al. | |
| 2009/0309711 A1 | 12/2009 | Adappa et al. | |
| 2010/0010689 A1 | 1/2010 | Yasushi et al. | |
| 2010/0108425 A1 | 5/2010 | Crespo et al. | |
| 2010/0234064 A1 | 9/2010 | Harris | |
| 2010/0268425 A1 | 10/2010 | Pettersson et al. | |
| 2010/0274411 A1 | 10/2010 | Ozaki | |
| 2010/0310011 A1 | 12/2010 | Sexton et al. | |
| 2011/0079073 A1 | 4/2011 | Keays | |
| 2011/0304465 A1 | 12/2011 | Boult et al. | |
| 2011/0308297 A1 | 12/2011 | Tsuzuki et al. | |
| 2012/0020837 A1 | 1/2012 | Withrow et al. | |
| 2012/0075094 A1 | 3/2012 | Keays | |
| 2012/0157871 A1 | 6/2012 | Walden et al. | |
| 2012/0330175 A1 | 12/2012 | Phillips et al. | |
| 2013/0021153 A1 | 1/2013 | Keays | |
| 2013/0035602 A1 | 2/2013 | Gemer | |
| 2013/0111979 A1 | 5/2013 | Park | |
| 2013/0123570 A1* | 5/2013 | Ly | A61M 21/02 600/27 |
| 2013/0150727 A1 | 6/2013 | Phillips et al. | |
| 2013/0282321 A1 | 10/2013 | Son et al. | |
| 2013/0305808 A1 | 11/2013 | Yoo | |
| 2014/0012143 A1 | 1/2014 | Gilbert et al. | |
| 2014/0062703 A1 | 3/2014 | Purks et al. | |
| 2014/0062722 A1* | 3/2014 | Ofir | G01N 27/26 340/870.02 |
| 2014/0210627 A1 | 7/2014 | Nothacker et al. | |
| 2014/0303836 A1 | 10/2014 | Phelan | |
| 2014/0311215 A1 | 10/2014 | Keays et al. | |
| 2014/0361900 A1 | 12/2014 | Nothacker et al. | |
| 2014/0371603 A1 | 12/2014 | Fujita et al. | |
| 2015/0084774 A1 | 3/2015 | Wojcik et al. | |
| 2015/0164416 A1 | 6/2015 | Nothacker et al. | |
| 2015/0251660 A1 | 9/2015 | Nelson | |
| 2015/0325104 A1 | 11/2015 | Greenhut et al. | |
| 2015/0359469 A1 | 12/2015 | Jacobs et al. | |
| 2015/0360696 A1 | 12/2015 | Yi et al. | |
| 2016/0021228 A1 | 1/2016 | Roberts | |
| 2017/0086714 A1 | 3/2017 | Nothacker et al. | |
| 2018/0086264 A1 | 3/2018 | Pedersen | |
| 2019/0246958 A1 | 8/2019 | Moeller et al. | |

* cited by examiner

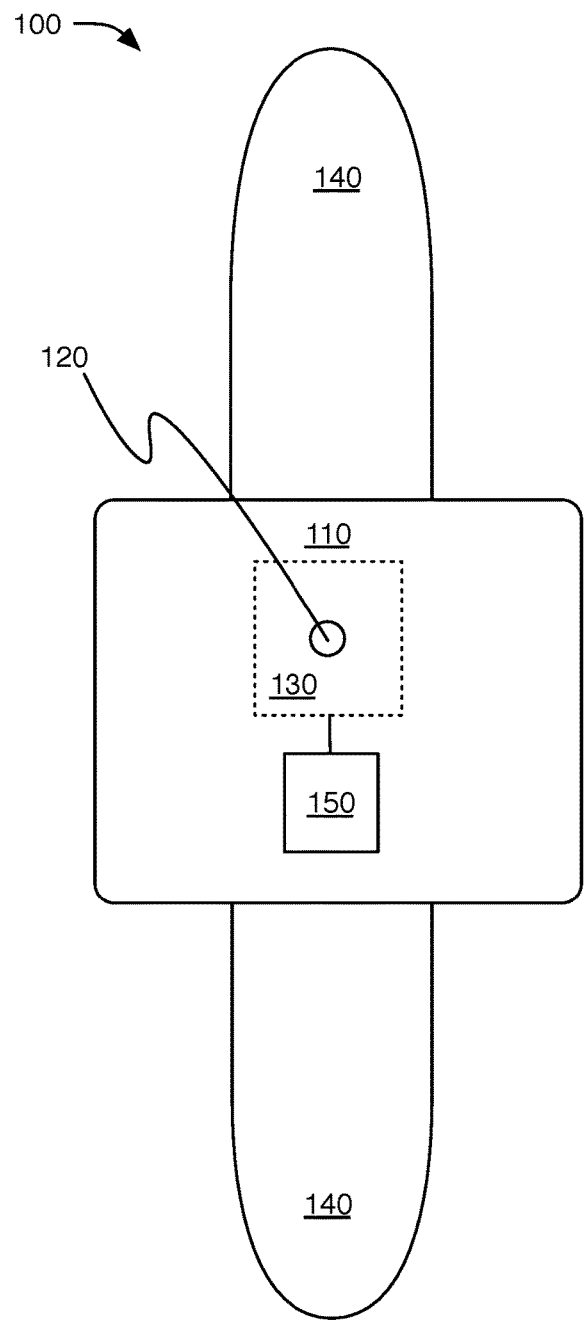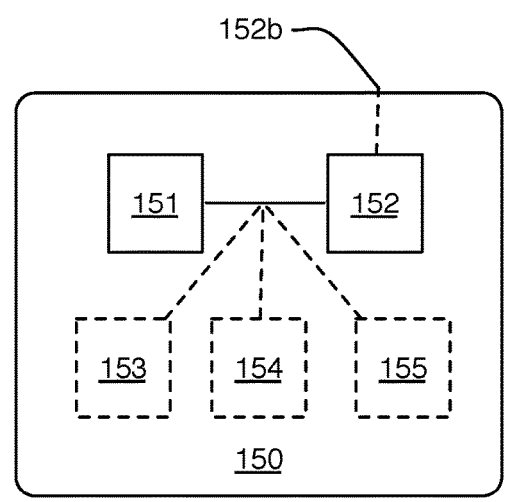
FIGURE 1A
FIGURE 1B

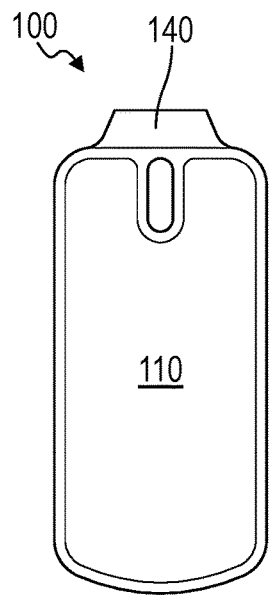
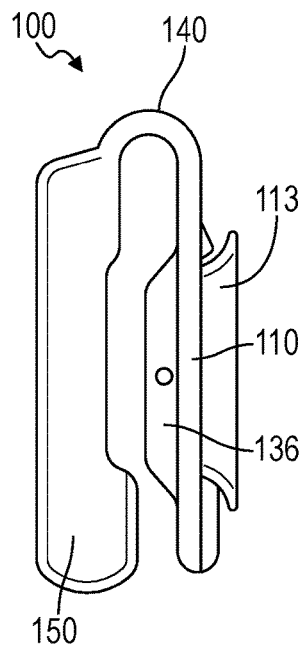
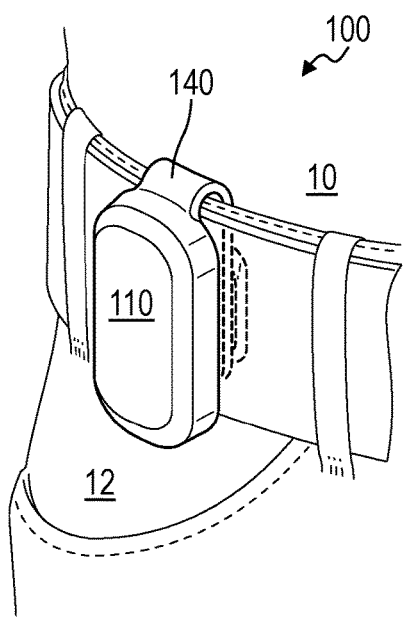
FIGURE 6A     FIGURE 6B     FIGURE 6C
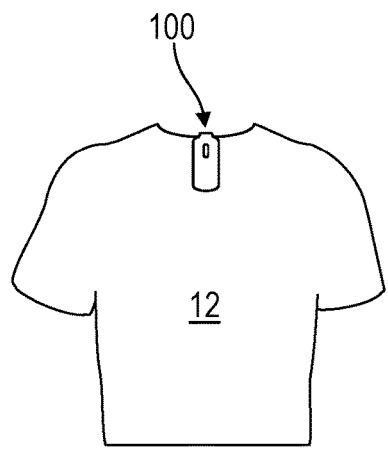
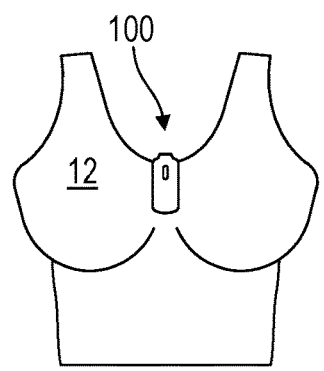
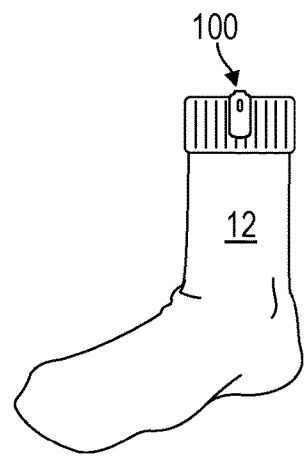
FIGURE 6D     FIGURE 6E     FIGURE 6F

WEARABLE SYSTEM AND METHOD FOR MONITORING INTOXICATION

CROSS-REFERENCE TO RELATED APPLICATIONS

This application is a continuation of U.S. application Ser. No. 15/666,062, filed 1 Aug. 2017, which is a continuation of U.S. application Ser. No. 15/375,801, filed 12 Dec. 2016, now issued as U.S. Pat. No. 9,788,772, which claims the benefit of U.S. Provisional Application No. 62/269,854, filed 18 Dec. 2015, and is a continuation-in-part of U.S. application Ser. No. 15/294,317, filed on 14 Oct. 2016, which is a continuation of U.S. application Ser. No. 14/925,675, filed 28 Oct. 2015, which is a continuation of U.S. application Ser. No. 14/631,125, filed 25 Feb. 2015, which is a continuation-in-part of U.S. application Ser. No. 14/470,376 filed 27 Aug. 2014, which is a continuation of U.S. patent application Ser. No. 14/169,029, filed 30 Jan. 2014, which claims the benefit of U.S. Provisional Application Ser. No. 61/812,704 filed 16 Apr. 2013 and U.S. Provisional Application Ser. No. 61/759,390 filed 31 Jan. 2013, which are each incorporated in their entirety herein by this reference.

TECHNICAL FIELD

This invention relates generally to the intoxication monitoring field, and more specifically to a new and useful system and method for monitoring intoxication.

BACKGROUND

Alcohol use remains the third leading cause of death both in the USA (85,000 deaths annually) and worldwide (up to 2.5 million deaths annually). The economic costs associated with excessive drinking exceed $223 billion annually in the USA alone. Some of the objective methods for measuring alcohol, such as breathalyzers and biological assays, can have significant drawbacks, such as invasiveness, constant user interaction, and/or the inability to provide real-time (or near real-time) quantitative measurements of alcohol (e.g., as opposed to metabolites). Thus, there is a need in the intoxication monitoring field to create an improved intoxication monitoring system and method.

This invention creates such a new and useful intoxication monitoring system and method.

BRIEF DESCRIPTION OF THE FIGURES

FIG. 1A is a schematic diagram of a variation of the system;

FIG. 1B is a schematic diagram of a variation of the electronics subsystem;

FIGS. 6A and 6B are a front view and side view, respectively, of a first example of a fourth embodiment of the system;

FIGS. 6C-6F are perspective views of the fourth embodiment of the system worn by a user on various clothing articles;

FIG. 7A is a front view of a first example of a fifth embodiment of the system;

FIGS. 7B and 7C are front views of a second and third example, respectively, of the fifth embodiment;

FIG. 8A is a front view of a second and third example of the fourth embodiment of the system;

FIG. 8B is a side view of a fourth and fifth example of the fourth embodiment of the system;

DESCRIPTION OF THE PREFERRED EMBODIMENTS

Figure 2A:
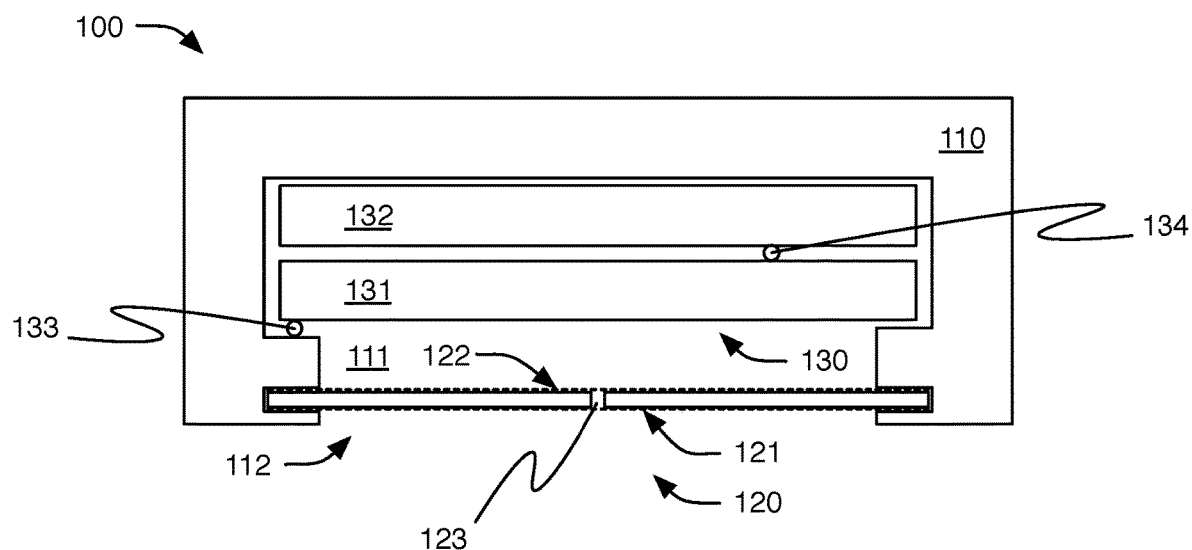
FIG. 2A is a cross-sectional view of the housing, inlet, and sensor of a first embodiment of the system.

The following description of the preferred embodiments of the invention is not intended to limit the invention to these preferred embodiments, but rather to enable any person skilled in the art to make and use this invention.

1. Overview.

As shown in FIG. 1A, a system 100 for monitoring intoxication of a user 10 preferably includes: a housing 110, an inlet 120, a sensor 130, a fastener 140, and an electronics subsystem 150. The system 100 can function to enable transdermal measurements of the user's blood alcohol content by sensing alcohol (i.e., ethanol) near a user's skin, preferably continuously and in near real time. Transdermal alcohol detection, which measures alcohol permeating through the skin and correlates that measurement to the blood alcohol concentration, can offer the capacity to provide a noninvasive, continuous, and quantitative measurement of bodily alcohol.

The system 100 can be configured to implement or facilitate implementation of one or more of the methods described in Section 3 below. Additionally or alternatively, the system 100 can be configured to implement any other suitable method, some embodiments, variations, and examples of which are described in U.S. application Ser. No. 15/294,317 filed on 14 Oct. 2016, U.S. application Ser. No. 14/470,376 filed 27 Aug. 2014, U.S. application Ser. No. 14/602,919, and U.S. application Ser. No. 15/205,876, which are each incorporated herein in their entireties by this reference.

2. System.

2.1 Housing.

Figure 7D:
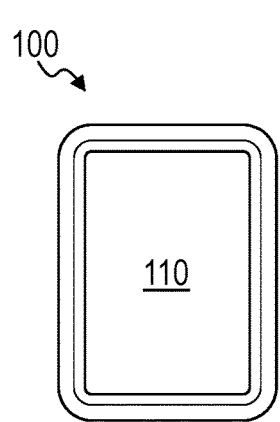
FIG. 7D is a perspective view of four examples of the fifth embodiment, each worn by a user.
Figure 7D:
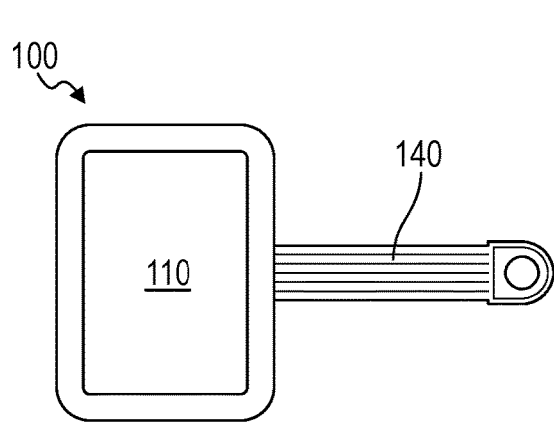
Figure 7D:
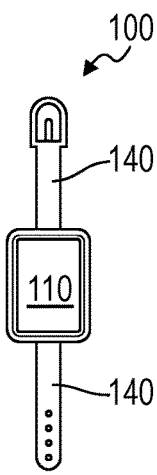
Figure 7D:
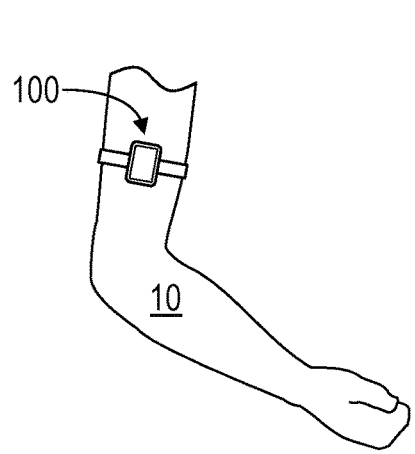
Figure 7D:
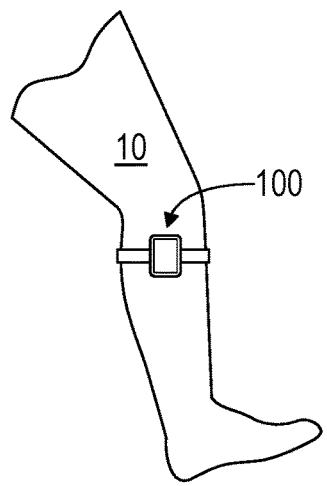
Figure 7D:
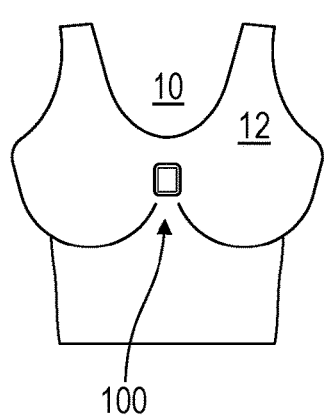
Figure 7D:
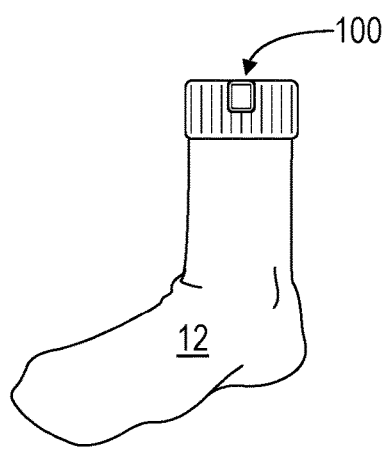
Figure 8C:
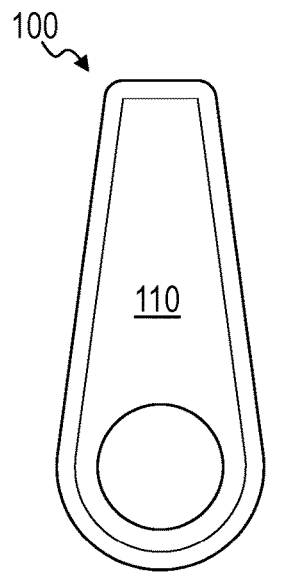
FIG. 8C is a perspective view of a portion of a sixth and seventh example of the fourth embodiment of the system.
Figure 8C:
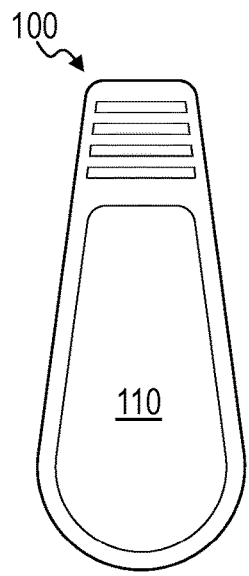
Figure 8C:
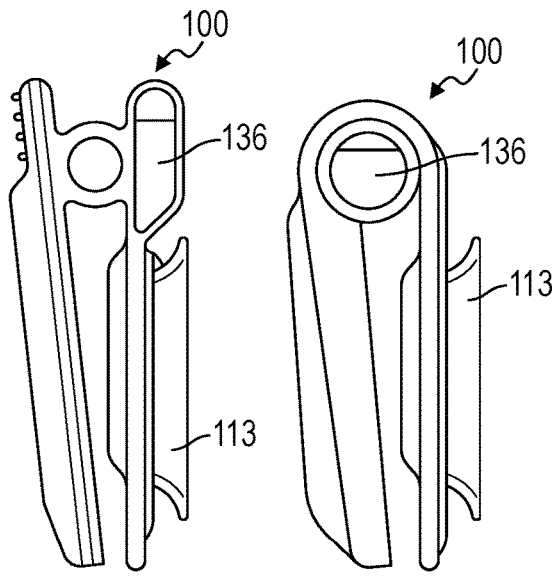
Figure 8C:
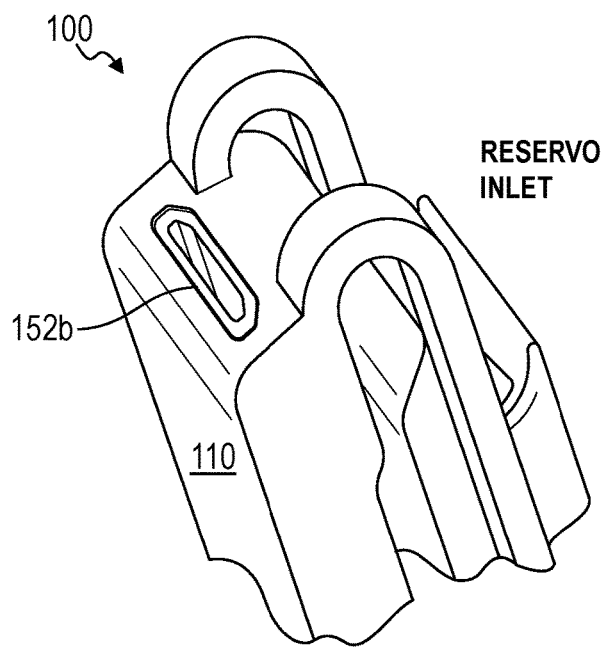
Figure 8C:
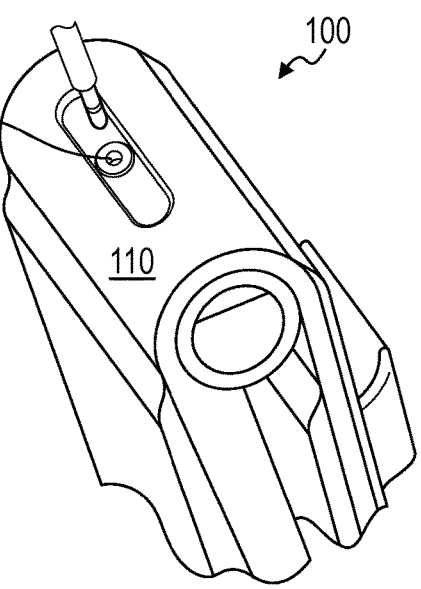
Figure 9A:
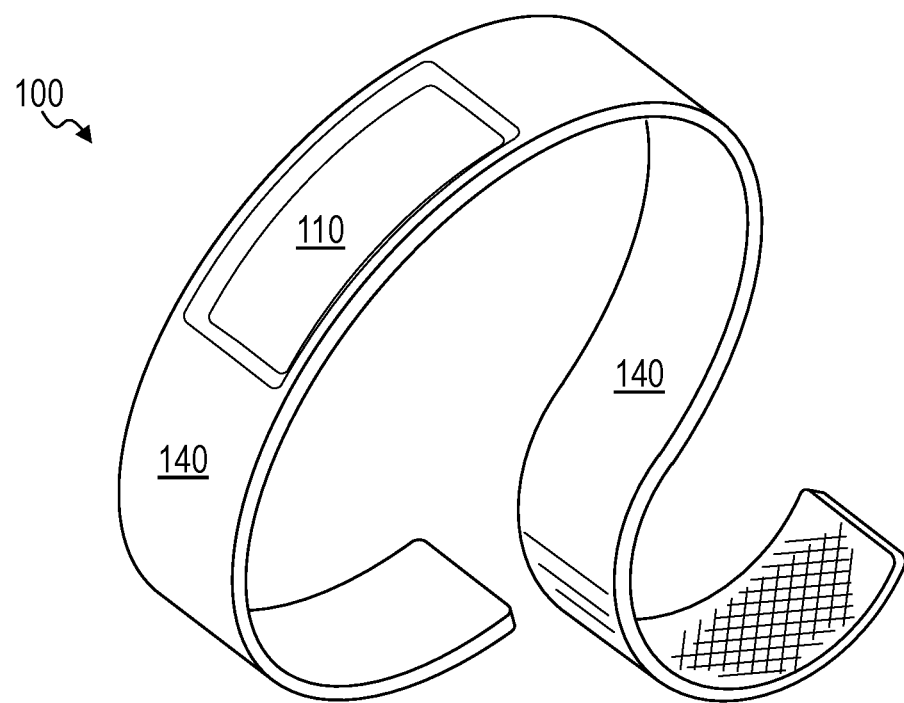
FIG. 9A is a perspective view of a sixth embodiment of the system including a color-changing display element.
Figure 9B:
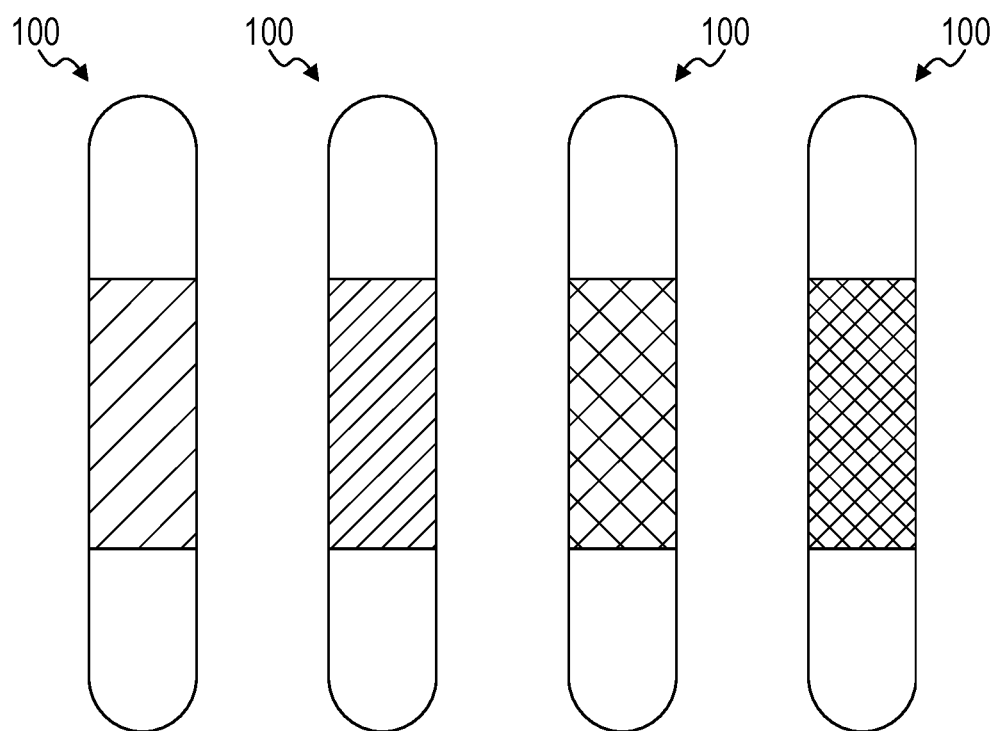
FIG. 9B is a front view of the sixth embodiment, displaying four different colors.
Figure 10A:
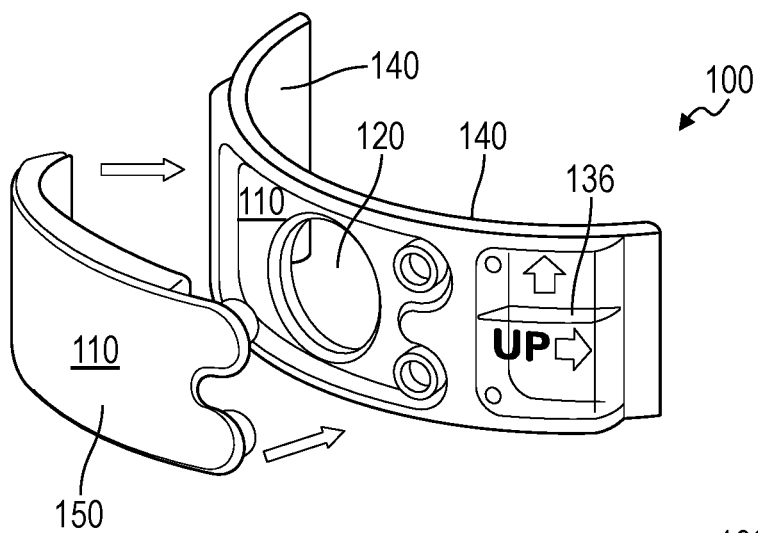
FIGS. 10A and 10B are a perspective view and a side view, respectively, of a seventh embodiment of the system.
Figure 10B:
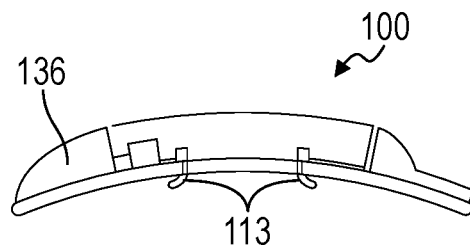
Figure 10C:
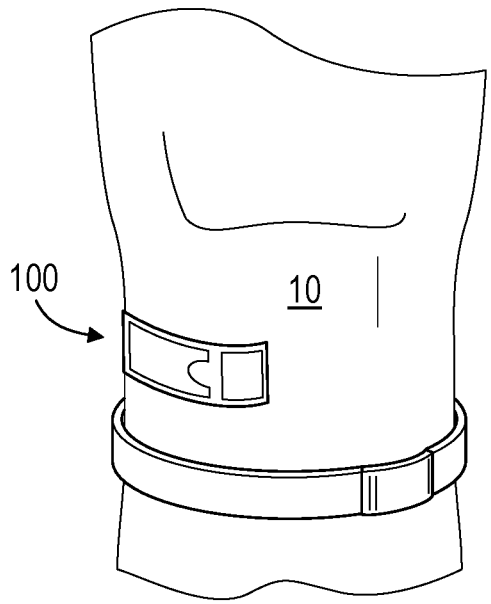
FIGS. 10C and 10D are each a perspective view of the seventh embodiment of the system adhered to a user.
Figure 10D:
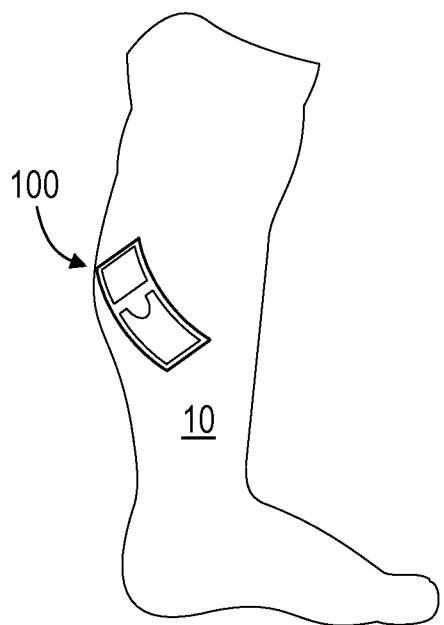
Figure 11A:
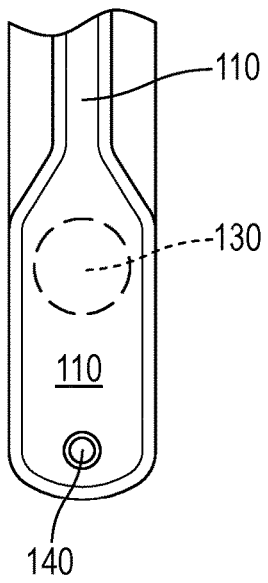
FIGS. 11A and 11B are a partial top view and a perspective view, respectively, of an eighth embodiment of the system.
Figure 11B:
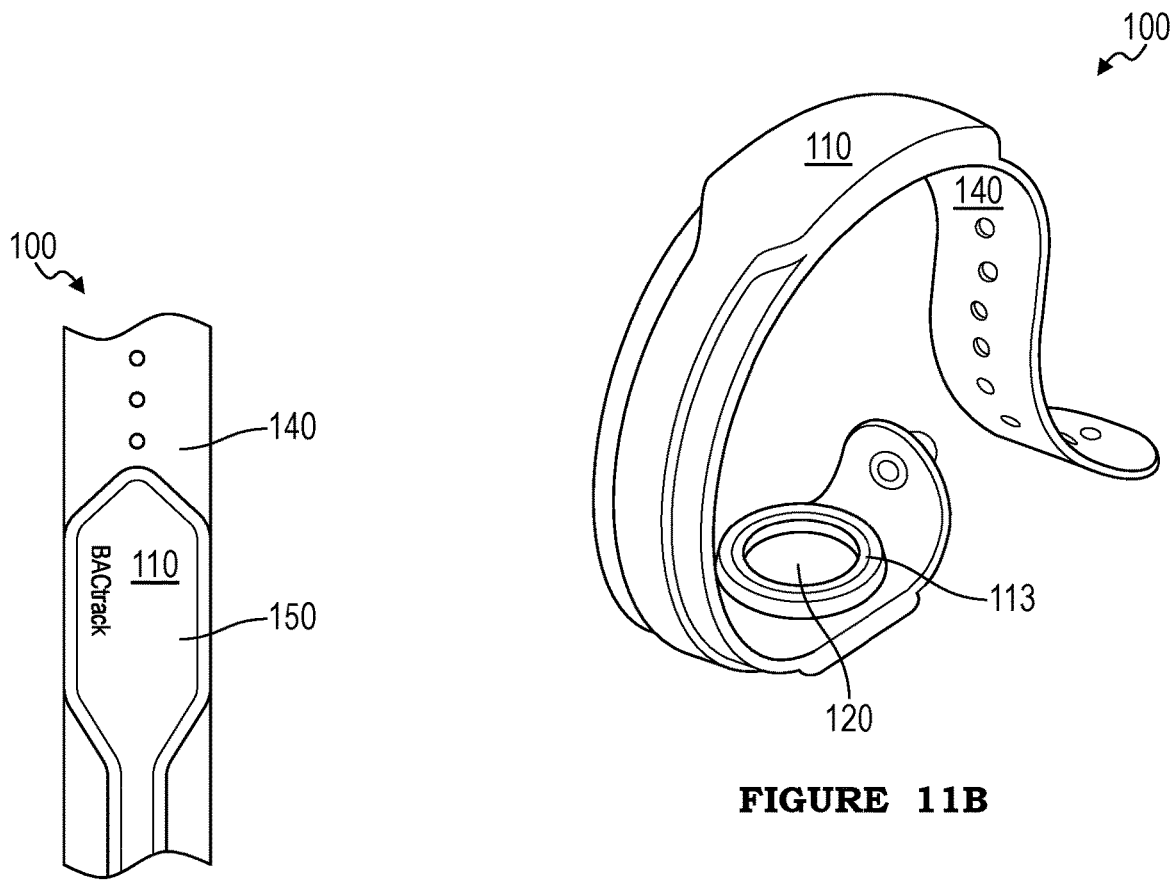
Figure 11C:
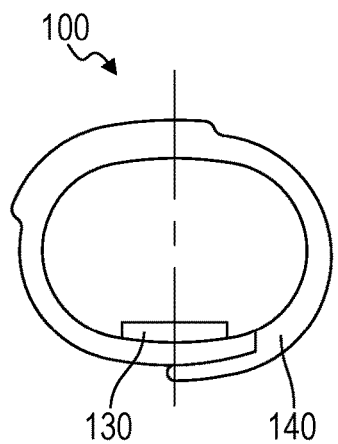
FIGS. 11C and 11D are side views of the eighth embodiment in two fastened conformations, configured to encircle a larger and smaller wrist, respectively.
Figure 11D:
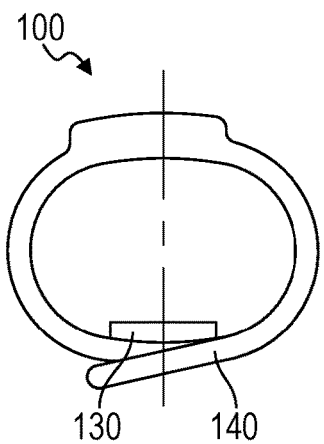
Figure 12A:
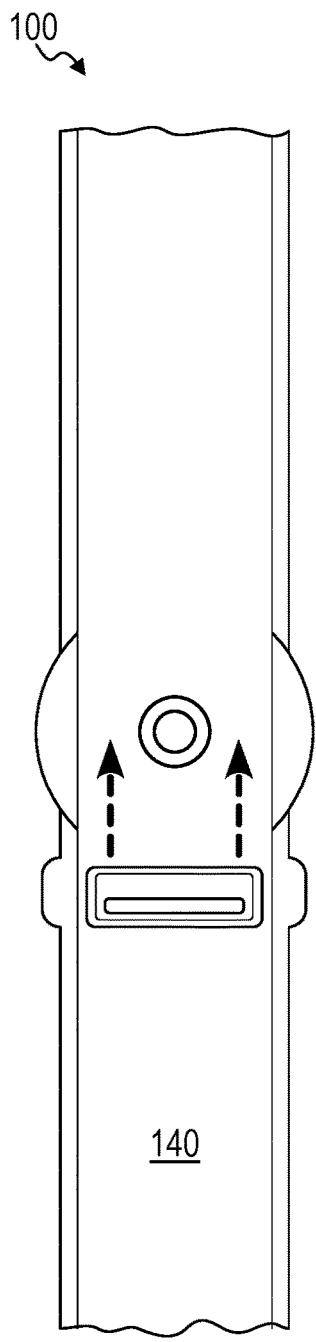
FIGS. 12A and 12B are a top view and a perspective view, respectively, of a ninth embodiment of the system.
Figure 12B:
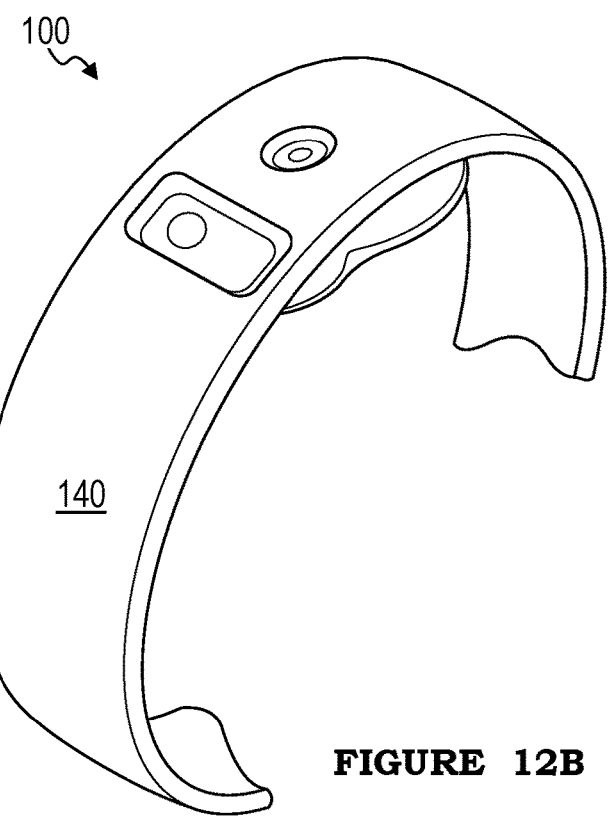
Figure 12C:
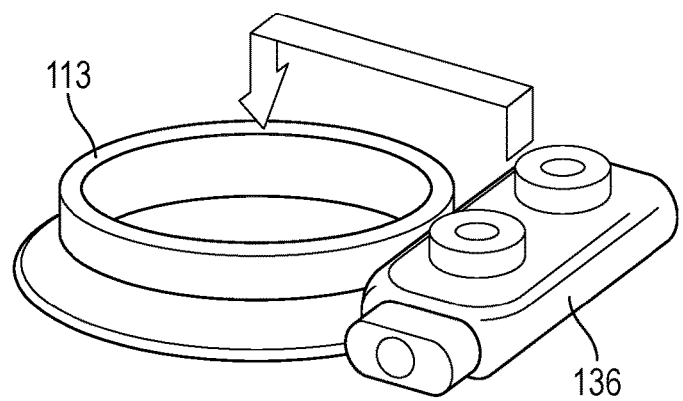
FIG. 12C is a perspective view of a replaceable portion of the ninth embodiment.
Figures 15A, 15B, 15C:
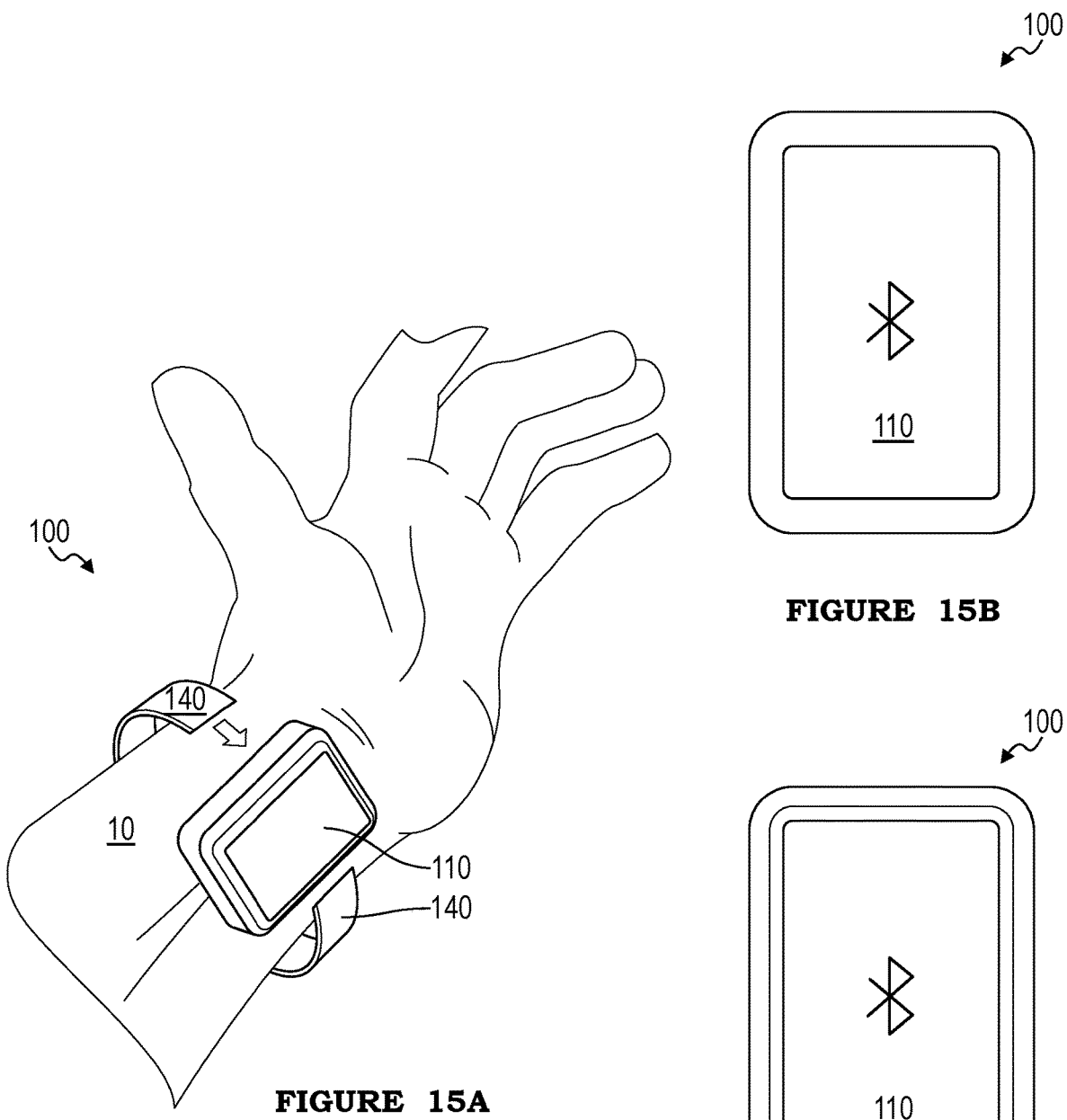
FIG. 15A is a perspective view of an example of a twelfth embodiment of the system worn by a user.
FIGS. 15B and 15C are perspective views of two examples of the twelfth embodiment.

The housing 110 functions to retain and/or protect the system components (e.g., as shown in FIGS. 7A and 15B-15C) and to position the sensing components (e.g., inlet 120, sensor 130) relative to each other and the user. The housing 110 is preferably rigid (e.g., made of or including a rigid polymer, metal, and/or other rigid material), but can alternatively be partially or entirely flexible. The housing 110 can include a low allergic response material (e.g., at a surface configured to contact the skin of the user, to minimize allergic reactions caused by wearing the system 100). The housing 110 materials can be opaque, transparent, and/or translucent (e.g., to allow viewing of internal components, to enable conduction of light transmitted by system components, etc.).

The housing 110 can define an analysis volume 111, preferably a sealed analysis volume (e.g., wherein the volume is fluidly isolated from the ambient environment and/or from an outer side 122 of the inlet, etc.) but alternatively a volume open to the ambient environment (e.g., through the inlet 120, through an outlet, such as an outlet opposing the inlet 120 or in any other suitable position, etc.). In a first embodiment (e.g., as shown in FIG. 2A), the housing 110 defines a cavity, retains the sensor 130 within the cavity, and retains the inlet 120 at or near the opening of the cavity, preferably such that the inlet 120 is the only (or substantially only) fluidic path into the cavity from the ambient environment. The cavity can be defined by a piece (e.g., the housing 110, a portion of the housing 110, etc.) of unitary construction (e.g., wherein the inlet 120 is sealed to the piece, or wherein the inlet 120 and the piece are of unitary construction, etc.), or can be defined by multiple sealed or otherwise physically coextensive pieces (e.g., a first piece, such as a barrel, retaining the inlet 120, sealed to a second piece, such as a cap, retaining the sensor 130; a first piece retaining both the inlet 120 and sensor 130 sealed by a second piece; etc.). In a first variation of this embodiment, the housing 110 retains the inlet 120 and sensor 130 apart from each other in position (e.g., the sensor 130 retained within the housing 110, and the inlet 120 adhered to the housing exterior), and can thereby define an analysis volume 111 between the sensor 130 and an inner side 121 of the inlet. In a second variation, the inlet 120 is retained against the sensor 130 (e.g., adhered to the sensor 130, pressed against the sensor 130 by the housing 110, positioned at the sensor 130 by the housing 110, etc.). In variations, the analysis volume 111 can have a volume from 0.1 µL to 10 mL. Alternatively, the analysis volume 111 can be substantially zero (e.g., wherein the inlet 120 directly contacts the sensor 130).

The housing 110 can additionally or alternatively be operable to define a sampling volume 112 between the user 10 (e.g., a skin surface 11 of the user 10) and the inlet 120. The sampling volume 112 is preferably fluidly isolated from the analysis volume, and can additionally or alternatively be fluidly isolated from or fluidly coupled to the ambient environment (e.g., when the housing 110 is fastened to or otherwise retained against the skin surface 11). In variations, the sampling volume 112 can have a volume from 0.1 µL to 10 mL. Furthermore, the elements of the system 100 can have any suitable morphology that improves function of sensing functions of the sensor 130, as described below. For instance, the analysis volume 111 and/or sampling volume 112 can have a morphology that drives a sample from the user's skin toward the sensor 130 (e.g., from the skin toward the inlet 120, through the inlet 120, from the inlet 120 toward the sensor 130, etc.). In examples, the morphology can include a tapered portion (e.g., conical, arcuate, stepped, etc.; wherein the volume narrows toward the sensor), fluidic channels (e.g., urging fluid movement through the channels), elements that promote directed fluid flow due to pressure and/or thermal gradients (e.g., a thermal gradient created by heat from the user), and/or any other suitable elements. Additionally or alternatively, the system can include one or more active elements, such as pumps and/or fans, that drive the sample from the user's skin toward the sensor 130. However, the sensor 130 can additionally or alternatively be retained in position relative to the inlet 120 in any other suitable manner, and/or the analysis volume can be configured in any other suitable manner.

In one embodiment, the system 100 (e.g., the housing 110, the inlet 120, etc.) includes a gasket 113 arranged to contact (and preferably form a seal with) the skin surface 11 when the system 100 is worn (e.g., gasket 113 attached to a broad face of the housing 110 and surrounding the inlet 120). For example (e.g., as shown in FIGS. 3A-B and 4A-D), the gasket 113 can oppose the analysis volume across the inlet 120 (e.g., across a microporous membrane of the inlet, proximal the outer side 122 of the inlet), and the fastener 140 can be configured to retain the gasket 113 against the skin surface 11. In a first variation of this embodiment, the gasket 113 is operable to seal the sampling volume (cooperatively with the skin surface 11). In a second variation, the gasket 113 includes one or more vents/outlets, which function to enable air circulation within the sampling volume (e.g., to promote user comfort, to enhance sensor function) and/or reduce moisture retention/condensation within the sampling volume. In examples of this variation, the vents of the gasket 113 can be configured about a peripheral region of the gasket and/or configured in any other suitable manner. However, the housing 110, inlet 120, and/or any other component of the system can include any other suitable seal located in any other suitable position, or not include a seal, additional variations of which are shown in FIGS. 28A-28C and 29A-29C.

The housing 110 can additionally or alternatively retain the other system components (e.g., fastener 140, electronics subsystem 150, etc.) within an internal volume of the housing 110, and/or relative to the user. The components can be retained within the housing 110, can be retained external to the housing, or can additionally or alternatively be partially retained within the housing. In one variation, one or more elements can be retained within the housing 110, under a transparent casing of the housing 110 (e.g., to allow a user to view the component and/or light emitted by the component, such as a display, light emitting diode, or other indicator), at an exterior surface of the housing 110 (e.g., to allow physical contact with the component, such as an electrical power and/or data connector or a touch-sensitive control; to allow a user to view the component and/or light emitted by the component; etc.), attached (and/or attachable) to the housing 110, and/or retained in any other suitable arrangement. Additionally or alternatively, one or more portions of the housing 110 can be substantially opaque, such that elements within the housing are not visible from outside of the housing 110.

The housing 110 can additionally or alternatively function to maintain sensor environment conditions. For example, the housing 110 can include a thermally insulating material (e.g., to minimize temperature changes of the sensor 130), a water-absorptive element (e.g., to minimize water interaction with the sensor 130), and/or any other suitable environmental control. However, the housing 110 can additionally or alternatively have any other suitable configuration and include any other suitable elements.

2.2 Inlet.

The inlet 120 preferably functions to allow controlled ingress of one or more analytes from the user's body, such as ethanol, toward the sensor 130 (e.g., to the sensor 130, to the analysis volume 111, etc.), and can additionally or alternatively function to prevent contaminant ingress toward the sensor 130 and/or control (e.g., promote, prevent, etc.) water uptake by the sensor 130. The inlet 120 preferably defines an outer side 121 (e.g., ambient environment and/or sampling volume side) and an inner side 122 (e.g., analysis volume side) opposing the outer side 121 across the inlet 120. The inlet 120 can cooperate with one or more apertures 123 (e.g., includes a barrier layer defining an aperture), which function to allow or otherwise control sample ingress, through the inlet 120 into the analysis volume and towards the sensor 130, and one or more membranes 124, which function to minimize obstruction of the aperture(s) 123 and/or prevent ingress of solids, liquids, and/or undesired vapors.

The aperture 123 is preferably formed by removing material (e.g., laser-drilling, milling, etching, or otherwise removing material from an element such as a barrier layer), but can additionally or alternatively be formed by joining pieces (e.g., joining two pieces with semicircular gaps along an edge, etc.) or in any other suitable way. In variations that include a barrier layer defining the aperture 123, the barrier layer is preferably made of a rigid material (e.g., metal such as stainless steel, rigid polymer, etc.), but can additionally or alternatively include any other suitable material. In variations, the aperture 123 can be defined through a surface of the housing 110; however, the aperture 123 can additionally or alternatively be defined by any other element(s) of the system 100. In alternative examples, the aperture 123 can be a single hole, an array of holes, a screen, a porous barrier (e.g., microporous barrier), a diffusive barrier (e.g., material allowing diffusion of the analyte and/or other species across the barrier, such as silicone), and/or any other suitable aperture 123 configured to limit the ingress of the analyte and/or other species. Furthermore, the aperture(s) can have a fixed opening size, or can alternatively be adjustable in size to control the amount of sample entering the system for analysis.

The aperture 123 preferably limits the rate of analyte (and/or other species) ingress toward the sensor 130, which can function to minimize spurious signals due to changing user perspiration rates (e.g., due to exertion) and/or system movement (e.g., with respect to the skin surface 11). The aperture cross-sectional dimensions (e.g., diameter of a circular aperture, side, diagonal length of a rectangular aperture, etc.) are preferably micron-scale (e.g., 0.01 mm, 0.025 mm, 0.05 mm, 0.1 mm, 0.2 mm, 0.3 mm, 0.5 mm, 0.05-0.1 mm, 0.03-0.2 mm, etc.), but can alternatively be larger (e.g., 1 mm, 2 mm, greater than 1 mm, etc.) or smaller. A micron-scale aperture can help limit ethanol ingress to an appropriate rate for the sensor 130.

Each membrane 124 is preferably a microporous membrane (e.g., microporous polytetrafluoroethylene membrane). Each of the membranes 124 is preferably vapor-permeable, and can be permeable to ethanol vapor (and/or vapor of any other suitable analyte). Furthermore, each of the membranes is preferably impermeable to liquids and solids; however, variations of the membranes can alternatively allow some material ingress. For instance, the membrane 124 can be impermeable or permeable to water. The membranes 124 can be hydrophilic or hydrophobic.

Figure 2B:
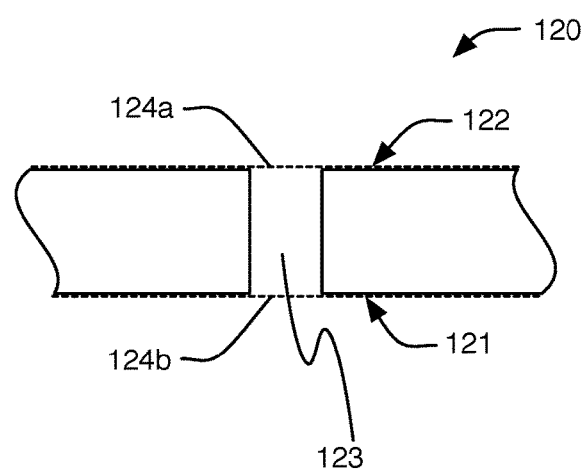
FIG. 2B is a detail cross-sectional view of the inlet of the first embodiment of the system.
Figure 3A:
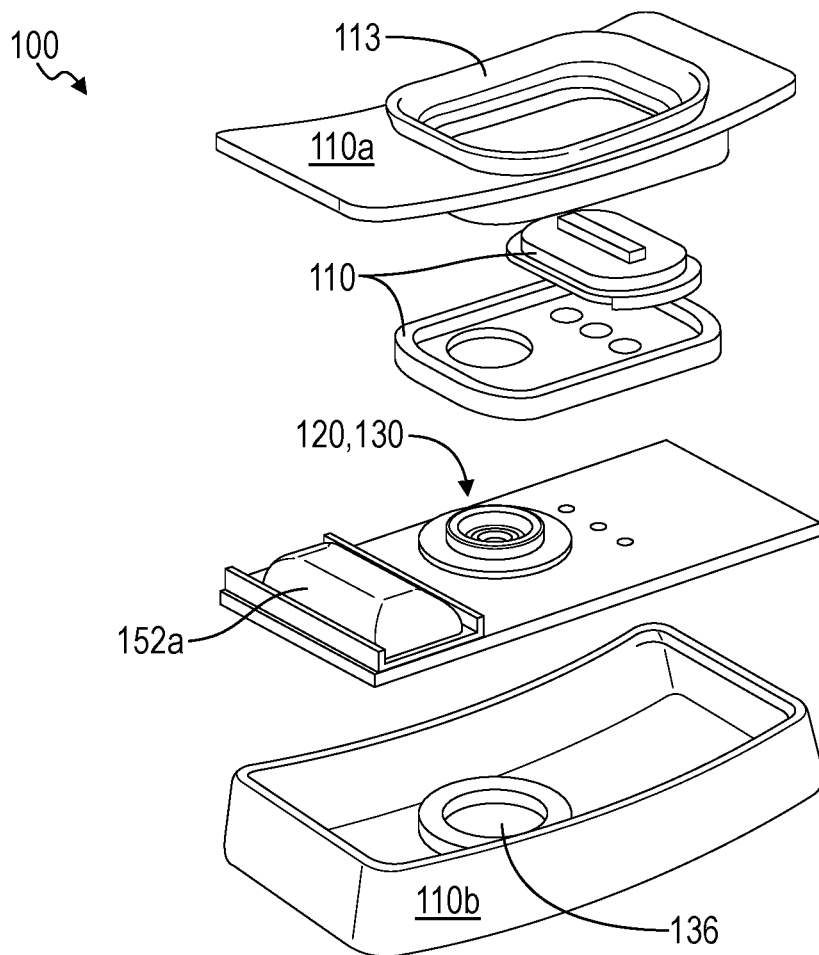
FIGS. 3A and 3B are an exploded view and a cross-sectional view, respectively, of the housing, inlet, and sensor of a second embodiment of the system.
Figure 3B:
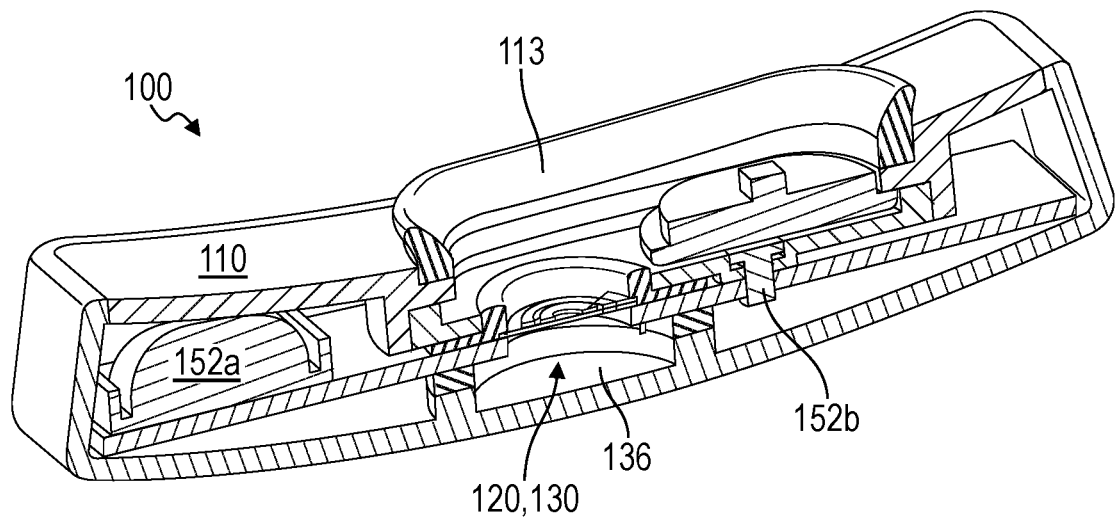
Figure 4A:
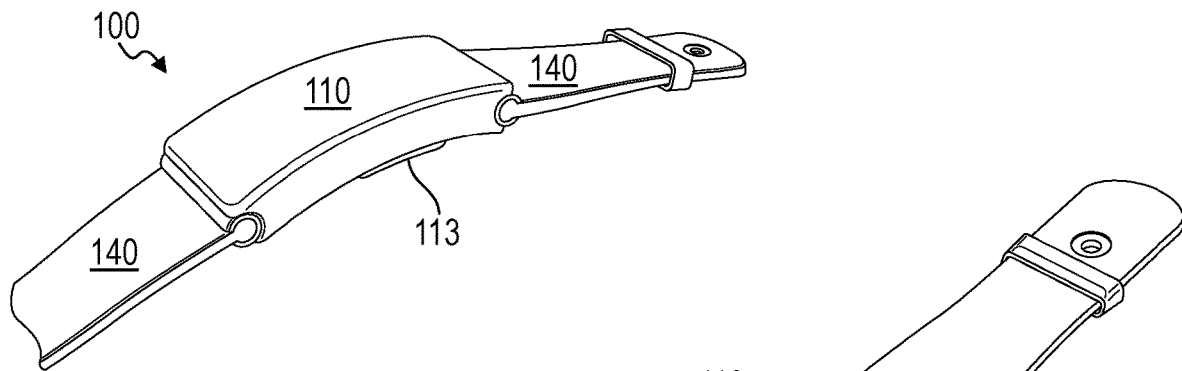
FIGS. 4A-4D are perspective views of a third embodiment of the system.
Figure 4B:
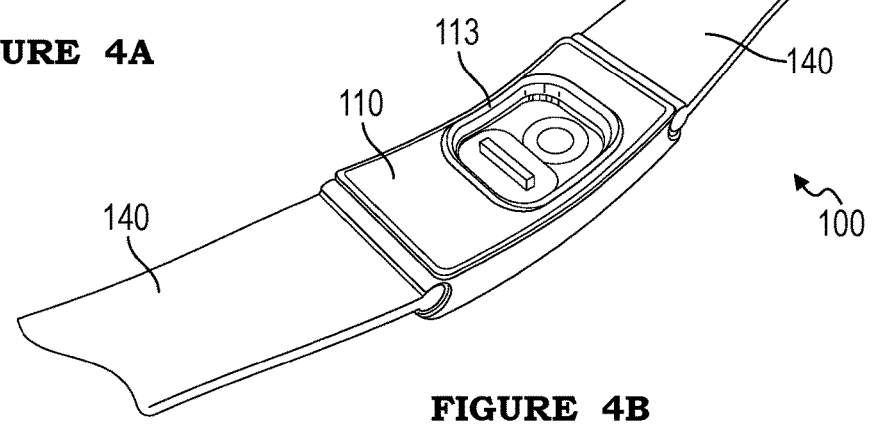
Figure 4C:
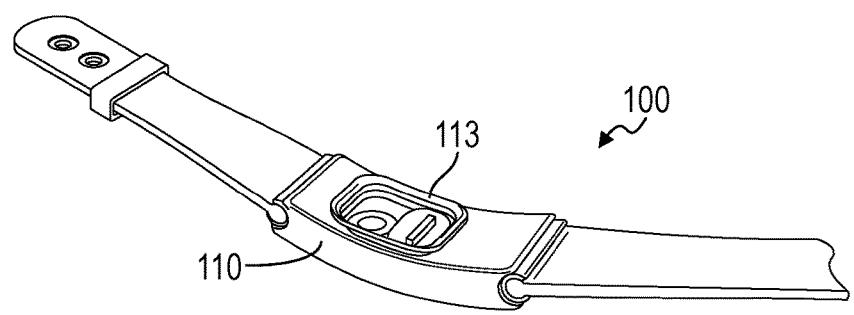
Figure 4D:
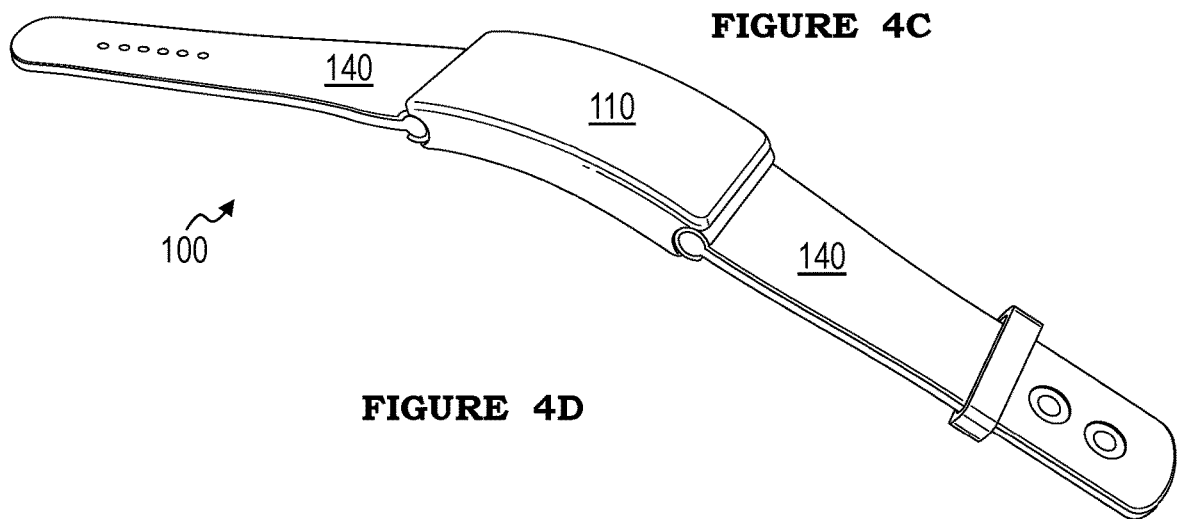
Figure 5A:
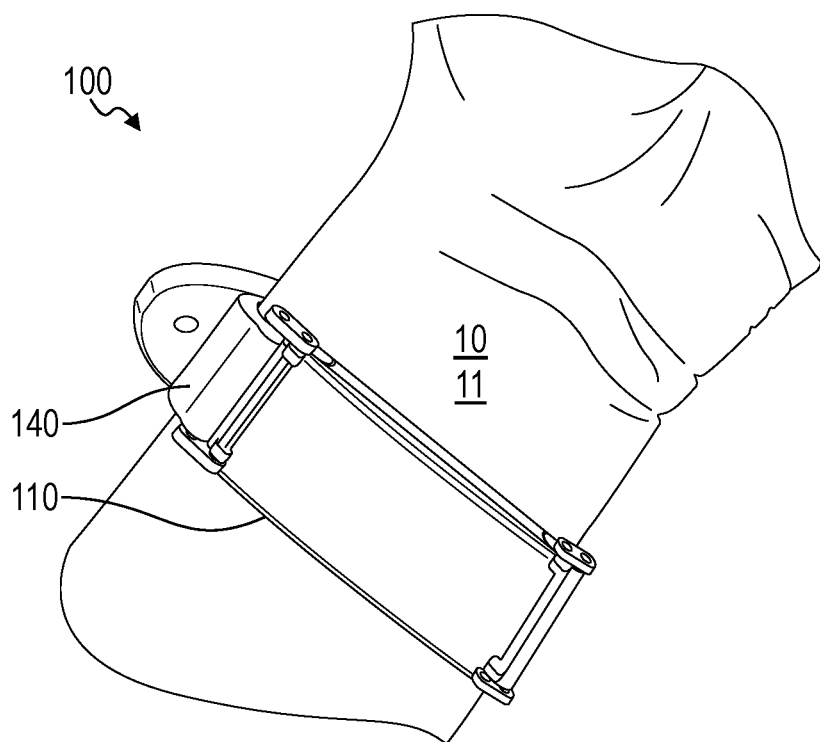
FIGS. 5A and 5B are perspective views of the third embodiment of the system worn by a user.
Figure 5B:
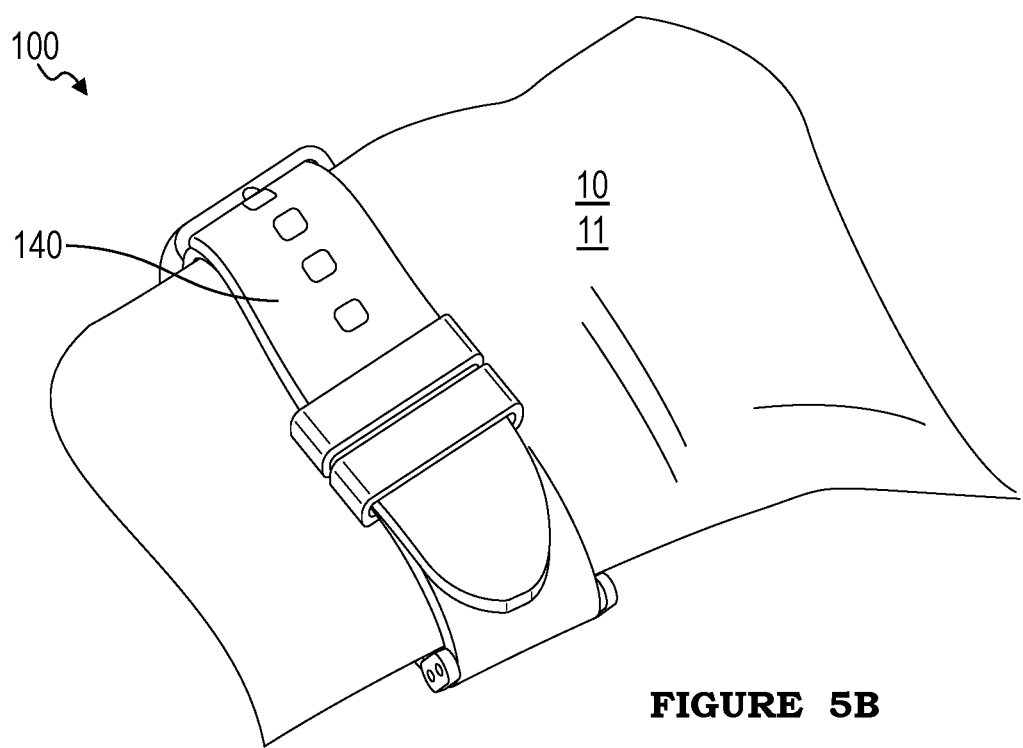

Each membrane 124 preferably covers the aperture 123 (e.g., is attached to the barrier layer surrounding the aperture 123). The inlet 120 can include one membrane 124 covering the outer 121 or inner side 122 of the aperture, two membranes 124 (e.g., one covering each of the aperture sides, as shown in FIG. 2B), or any other suitable number of membranes 124 in any other suitable arrangement. In variations that include a membrane 124 covering the inner side 122 ("inner membrane", 124a), the housing 110 (and/or other suitable component of the system) preferably fluidly isolates the entire inner membrane from the ambient environment and/or sampling volume 112, except for a possible fluidic path through the aperture 123 (e.g., to prevent the analyte and/or other species from reaching the analysis volume 111 without passing through the aperture 123, such as by lateral transit through the inner membrane beginning from an exposed edge of the inner membrane). Analogously, a membrane 124 covering the outer side 121 ("outer membrane", 124b) is preferably fluidly isolated from the analysis volume 111, except for a possible fluidic path through the aperture 123.

In one embodiment, at least one of the membranes 124 is adhesive (or includes an adhesive layer), and the inlet 120 is retained by the adhesive membrane (e.g., adhesive microporous polytetrafluoroethylene membrane). The adhesive membrane can be easily removable and/or replaceable by a user (e.g., allowing user replacement of the membrane(s) 124, the aperture 123, and/or any other elements of the inlet 120 and sensor 130), or can additionally or alternatively be designed to be replaced by a vendor when needed. In a first variation of this embodiment, the membrane 124 is adhered to the housing 110 (e.g., to a rim surrounding a cavity defined by the housing 110, to a lip within the cavity, to the inner sidewalls of the cavity, etc.). In a second variation, the membrane 124 is adhered to the sensor 130 (e.g., to a broad face of the primary wafer 131, preferably the face proximal the counter electrode 133). In a first example of this variation, the membrane 124 is adhered directly to the sensor 130. In a second example, a spacer (e.g., washer, standoff, etc.) is adhered to the sensor 130, and the membrane 124 is adhered to the spacer. The spacer can function to prevent mechanical damage of the inlet 120 and/or sensor 130 arising from direct contact (e.g., prevent an electrode such as the counter electrode 133 from puncturing the membrane 124). In examples including a spacer, the spacer can be made of or include a polymer, such as polypropylene, but can additionally or alternatively include metal, ceramic, and/or any other suitable material.

However, one or more membranes 124 can additionally or alternatively be arranged within the aperture 123 (e.g., filling the aperture 123 partially or entirely), or can have any other suitable arrangement with respect to the aperture 123 and other system elements.

2.3 Sensor.

The sensor 130 functions to sample the concentration of one or more analytes. The sensor 130 is preferably operable to detect alcohol (i.e., ethanol), but can additionally or alternatively be operable to detect any other suitable analyte. The analyte is preferably emitted by the user 10, but can additionally or alternatively come from any other suitable source. The sensor 130 is preferably arranged within the housing 110, as described in Section 2.1 above, and the analyte preferably travels from the user 10 to the sensor 130 through the inlet 120 (e.g., as described above). However, the sensor 130 can have any suitable arrangement.

The sensor 130 preferably includes a fuel cell configured to facilitate and/or quantify chemical reactions involving the analyte (e.g., as shown in FIG. 2A). The fuel cell can have three electrodes (e.g., a counter electrode 133 and a sensing electrode 134 configured to conduct and allow detection of current generated by the fuel cell, and a reference electrode 135 configured to provide a reference potential) but alternatively can be a two-electrode fuel cell (e.g., not include a reference electrode) or have any other suitable number of electrodes.

The fuel cell preferably includes a primary wafer 131 (e.g., through which protons can diffuse or be otherwise transported) or other fuel cell element configured to transport protons and/or other products of a reaction involving the analyte. The fuel cell preferably includes a single primary wafer 131 to which both the counter electrode 133 and the sensing electrode 134 are electrically connected or otherwise electrically coupled (e.g., to opposing sides of the primary wafer 131), but can alternatively include multiple primary wafers 131 (e.g., wherein the counter electrode 133 is electrically connected to a first side of a first primary wafer, the sensing electrode 134 is electrically connected to a first side of a second primary wafer, and the second sides of the two wafers are electrically connected to each other) or any other suitable reaction product transport elements. One or more of the sides of the primary wafer(s) 131 (e.g., the sides to which fuel cell electrodes are connected) preferably include a catalytic coating or other catalyst configured to catalyze the fuel cell reactions. The fuel cell electrodes can additionally or alternatively include or be made of a catalyst. The wafer and/or electrode catalyst preferably includes platinum, but can additionally or alternatively include any other suitable catalytic agent.

The fuel cell preferably includes one or more reservoir wafers 132. The reservoir wafer 132 can retain species involved in the fuel cell reactions (e.g., water), contaminants (e.g., unwanted species that enter the analysis volume 111 through the inlet 120), and/or any other suitable species. Alternative system configurations can include a liquid and/or vapor reservoir 136 configured to retain these species, and can additionally include sealing elements to minimize egress of the species from the reservoir 136, or otherwise promote a hydrated state of the reservoir 136. In fuel cells including a reservoir 136, the reservoir 136 is preferably fluidly coupled to one or more of the primary wafer surfaces (e.g., so that water can flow between the reservoir 136 and the surfaces). In one example, the reservoir 136 is arranged opposing the analysis volume 111 and/or inlet 120 across the primary wafer 131 (e.g., such that the primary wafer 131 directly contacts the reservoir 136). In a second example, the reservoir 136 is arranged apart from the primary wafer 131, and is fluidly coupled to the primary wafer 131 by one or more tubes, channels, and/or other fluid pathways (e.g., defined by the housing 110). In variations, the reservoir 136 can have a volume from 0.1 µL to 10 mL. However, the reservoir 136 can have any other suitable size, shape, and/or arrangement.

In one embodiment, as shown in FIG. 2A, the fuel cell includes a counter electrode 133 electrically coupled to a catalytic coating on a first side of a primary wafer 131, and a sensing electrode 134 electrically coupled to a catalytic coating on a second side of the primary wafer 131 opposing the first side. The counter electrode 133 is preferably maintained at a positive potential relative to the sensing electrode 134, but can alternatively be maintained at any suitable potential, or not be maintained at a specific potential. Ethanol incident upon the second side reacts (e.g., catalyzed by a catalytic coating) with water (e.g., from the counter-reaction, from the reservoir wafer 132, from air, etc.), producing ethanoic acid, protons, and electrons (e.g., as described by the chemical reaction $CH_3CH_2OH+H_2O \rightarrow CH_3COOH+4e^-+4H^+$). The generated protons travel through the primary wafer 131 to the first side, while the generated electrons travel from the sensing electrode 134, through a current sensor (e.g., circuit operable to quantify electrical current), to the counter electrode 133. At the first side, a counter-reaction occurs: the protons and electrons react (e.g., catalyzed by a catalytic coating) with oxygen (e.g., from air, such as air from the ambient environment and/or sampling volume 112 that travels through the inlet 120 to the sensor 130) to produce water (e.g., as described by the chemical reaction $O_2+4H^++4e^- \rightarrow 2H_2O$). The current sensor samples the current generated by the fuel cell, which is directly proportional to the amount of ethanol reacting at the fuel cell (and can therefore be correlated with the amount of transdermal ethanol reaching the sensor 130). The electrodes and catalytic coatings are preferably made of platinum, but can additionally or alternatively include any other suitable materials.

In a first variation of this embodiment, the fuel cell additionally includes a reference electrode 135 (e.g., platinum reference electrode). In this variation, the electric potential of the sensing electrode 134 can be maintained relative to the reference electrode 135 (e.g., maintained at a predetermined potential difference, such as 0 V, −0.1 V, −0.5 V, +0.25 V, etc.; maintained at a dynamically determined potential difference). This variation can enable a passive, noninvasive, and/or continuous measurement of transdermal alcohol, and can provide enhanced sampling speed, signal stability, and/or sensor longevity. In a second variation, the system includes a two-electrode fuel cell, an outlet through which the analyte can exit the analysis volume 111, and a pump operable to move the analyte through the analysis volume 111 and out the outlet. However, the fuel cell can include any suitable elements in any suitable arrangement.

Additionally or alternatively, the sensor 130 can include a sensor configured to detect resistance changes (e.g., of a silicon oxide or tin oxide sensor element) in response to the presence of alcohol vapor (or any other suitable analyte), and/or include any other suitable mechanism for detecting the analyte concentration.

2.4 Electronics Subsystem.

The electronics subsystem 150 preferably functions to power and control the sensor 130 and to receive, analyze, store, and/or transmit data sampled by the sensor 130. The electronics subsystem 150 preferably includes a processor 151 and a power module 152, and can additionally or alternatively include a communication module 153, display 154, light emitter 155, and/or any other suitable elements (e.g., as shown in FIG. 1B).

The processor 151 is preferably operable to continuously determine a time series of blood alcohol contents of the user based on a time series of signals received from the alcohol sensor. The samples can be collected automatically and/or manually, can be collected continuously and/or intermittently, and can be collected at regular and/or irregular intervals. The processor 151 can control system components to reduce system power consumption. For example, the processor 151 can alter the rate at which the sensor 130 samples the alcohol concentration (e.g., based on current and/or previous sensor data; user inputs; auxiliary information such as user location, user preferences, user history, etc.). In a specific example, when the sensor 130 indicates substantially no alcohol presence, the processor 151 can control the sensor 130 to reduce the sampling rate (e.g., to once every 0.5, 1, 2, 3, 5, 10, 20, 1-5, or 3-10 minutes). In this specific example, when alcohol is detected, the processor 151 can control the sensor 130 to increase the sampling rate (e.g., to sample as quickly as possible; to sample once every 0.1, 0.5, 1, 2, 3, 5, or 0.5-2 seconds). As such, the processor 151 can be operable to dynamically modulate a sampling rate associated with the sensor. However, the processor 151 can additionally or alternatively be operable in any other suitable way.

While aspects of the processor 151 are preferably implemented, at least in part, at the wearable device described above, one or more modules of the processor 151 can additionally or alternatively be implemented in one or more processing elements (e.g., hardware processing element, cloud-based processing element, etc.) not physically integrated with the wearable device, such that processing by the system 100 can be implemented in multiple locations and/or phases.

The power module 152 can function to power the processor 151, sensor 130, and/or any other suitable components of the system. The power module is preferably electrically coupled (e.g., connected by conductive wire) to the processor 151, sensor 130, and/or other powered system components, wherein the processor preferably controls power provision (e.g., through component operation mode control), but power provision and/or power module management can alternatively be performed by any other suitable component.

The power module 152 preferably includes a power source. The power source preferably includes a battery, and in variations can include one or more of a primary battery and a secondary battery. The power module 152 can additionally or alternatively include a capacitor (e.g., to facilitate fast discharging in combination with a battery), a fuel cell with a fuel source (e.g., metal hydride), a thermal energy converter (e.g., thermionic converter, thermoelectric converter, mechanical heat engine, etc.) optionally with a heat source (e.g., radioactive material, fuel and burner, etc.), a mechanical energy converter (e.g., vibrational energy harvester), a solar energy converter, and/or any other suitable power source. In variations of a power source 152 including a battery, the battery can have a lithium phosphate chemistry, lithium ion polymer chemistry, lithium ion chemistry, nickel metal hydride chemistry, lead acid chemistry, nickel cadmium chemistry, metal hydride chemistry, nickel manganese cobalt chemistry, magnesium chemistry, or any other suitable chemistry. The primary battery can have a lithium thionyl chloride chemistry, zinc-carbon chemistry, zinc chloride chemistry, alkaline chemistry, oxy nickel hydroxide chemistry, lithium-iron disulfide chemistry, lithium-manganese oxide chemistry, zinc-air chemistry, silver oxide chemistry, or any other suitable chemistry.

The power module 152 can additionally or alternatively include a power input. The power input preferably includes an electrical connector (e.g., jack, plug, etc.), but can additionally or alternatively include a wireless electrical power input (e.g., inductive power input) and/or any other suitable power input. The electrical jack is preferably electrically coupled to the battery, processor 151, and/or any other suitable component of the electronics subsystem, more preferably operable to receive an electrical power input and to transmit the electrical power input to the electronics subsystem. In a specific example, the electrical jack is retained at a surface of the housing 110, wherein the electrical jack is partially or entirely covered by the user 10 during normal wear of the system (e.g., the electrical jack is located on the same side of the housing as the inlet 120).

The communication module can function to communicate with external devices, such as a user device or remote computing system. The communication module can include a wireless communication module (e.g., radio) and/or a wired communication module. The wireless communication module can support one or more short-, medium-, and/or long-range communication protocols, such as cellular, WiFi, Bluetooth, BLE, NFC, and/or any other suitable wireless communication protocols. The wired communication module preferably includes an electrical connection and/or connector (e.g., USB, Ethernet, coaxial, etc.) configured to transmit data. In one example, the electrical connection is a wired connection to a wearable device 200 (e.g., through a fastener 140 coupled to the wearable device 200). In another example, the electrical connection is a wireless connection (e.g., Bluetooth LE connection) that allows for communication between the system 100 and another computing system (e.g., mobile computing device, personal computer, etc.).

The communication module can send information (e.g., sensor measurements, system status, etc.) and/or control instructions to the external devices, and/or can receive information and/or control instructions (e.g., configuration information such as user preferences, requests for sensor measurements, etc.) from the external devices. For example, the processor can be operable to control a user device such as a smartphone or wearable device 200 (e.g., forearm-mountable computing device) to provide an intoxication notification based on the time series of blood alcohol contents (e.g., sampled by and received from the sensor 130).

The display and/or light emitter can function to display sensor measurements (e.g., numeric value of user's blood alcohol content; indication of the blood alcohol content range, such as high, low, or none; etc.), system status (e.g., normal status, sensor malfunction, low battery, etc.), messages for the user 10 (e.g., motivational messages), and/or any other suitable information. For example, the light emitter can emit green light when no alcohol is detected, yellow when moderate amounts of alcohol are detected, and red when high amounts of alcohol are detected. However, the electronics subsystem 150 can include any other suitable elements, and perform any other suitable functions, some embodiments, variations, and examples of which are described in U.S. application Ser. No. 15/294,317 filed on 14 Oct. 2016, U.S. application Ser. No. 14/470,376 filed 27 Aug. 2014, U.S. application Ser. No. 14/602,919, and U.S. application Ser. No. 15/205,876, which are each incorporated herein in their entireties by this reference.

2.5 Fastener.

The fastener 140 functions to couple the system 100 to a user. The fastener 140 and housing 110 can be of unitary construction or otherwise physically coextensive, or can be otherwise connected, coupled, or couplable.

The fastener 140 is preferably operable to retain the outer side 121 of the inlet against or near a skin surface 11 of the user. For example, the fastener 140 can be coupled to the housing 110 and operable to position a microporous membrane 124 (e.g., outer side of the outer membrane) proximal the skin surface 11 (e.g., retaining the membrane 124 against the skin surface 11, retaining a nearby gasket 113 or face of the housing against the skin surface 11, etc.). In embodiments that include an electrical jack near the inlet 120 (e.g., both on the same broad face of the housing 110), the fastener 140 can be further configured to position the electrical jack proximal the skin surface.

The fastener 140 is preferably operably to be easily and/or repeatably fastened and unfastened manually by the user 10. In specific examples, the fastener 140 can include a latch, snap, buckle, clasp, hook-and-loop fastening mechanism, and/or any other suitable fastening mechanism, and/or can be operable to expand and contract (e.g., including an elastic element, such as an expansion band; including a deployment clasp, butterfly clasp, or other clasp that is physically coextensive when unclasped; etc.). Alternatively, the fastener 140 can require a key or other security mechanism to be fastened and/or unfastened, can have a tamper-evident fastening mechanism (e.g., wherein the fastener 140 is changed during unfastening, such that it has a different visual appearance upon refastening), and/or can include any other suitable security elements.

In a first embodiment, the fastener 140 includes a strap (or straps) operable to encircle a body part of the user, such as the wrist and/or forearm (e.g., as shown in FIGS. 5A-5B, 7B-7C, 9A-9B, 11A-11D, 12A-12C, and 15A). In this embodiment, the strap(s) can retain the inlet 120 near or against a skin surface 11 (e.g., skin surface 11 on the same body part or a nearby body part of the user). The straps are preferably connected to the housing 110 on or proximal opposing edges of the housing (e.g., a top edge and a bottom edge).

In a first variation of this embodiment, the fastener 140 and housing 110 are operable to cooperatively encircle the entire body part. In a first example of this variation, the fastener 140 includes two straps, each connected (e.g., at or near a first end of the strap) to the housing 110 proximal one edge of the housing, and operable to connect to each other (e.g., by a buckle, claw clasp, jewelry clasp, etc.; at or near a second end of the strap opposing the first end) to encircle the body part. In a second example, the fastener 140 includes a single strap (e.g., each end of the strap connected to one of the opposing edges of the housing), and the strap is operable to expand and contract (e.g., as described above).

In a second variation of this embodiment, the fastener 140 is operable to couple to (e.g., connect to) a wearable device 200 such as a forearm-mountable computing device and/or wristwatch (e.g., serving as the strap(s) of the watch or computing device), and when coupled, be operable to cooperatively encircle the entire body part with the housing 110 and the wearable device 200. In a first example of this variation, the sensor 130, electronics subsystem 150, and/or other system components can communicate with and/or receive power from (or send power to) the wearable device 200 through the fastener 140 (e.g., through an electrical connection in the strap). In a second example, the sensor 130, electronics subsystem 150, and/or other system components are electrically isolated from the computing device.

In a second embodiment, the fastener 140 is operable to retain the housing 110 on or within a wearable device 200 such as a wristwatch or forearm-mountable computing device. The inlet 120 is preferably retained on or proximal the skin surface 11 by the wearable device 200. In this embodiment, the fastener 140 can be removably and/or repeatably couplable to the wearable device 200, or can be substantially permanently coupled or couplable to the wearable device 200 (e.g., not easily uncoupled and/or recoupled by a user).

Figure 16:
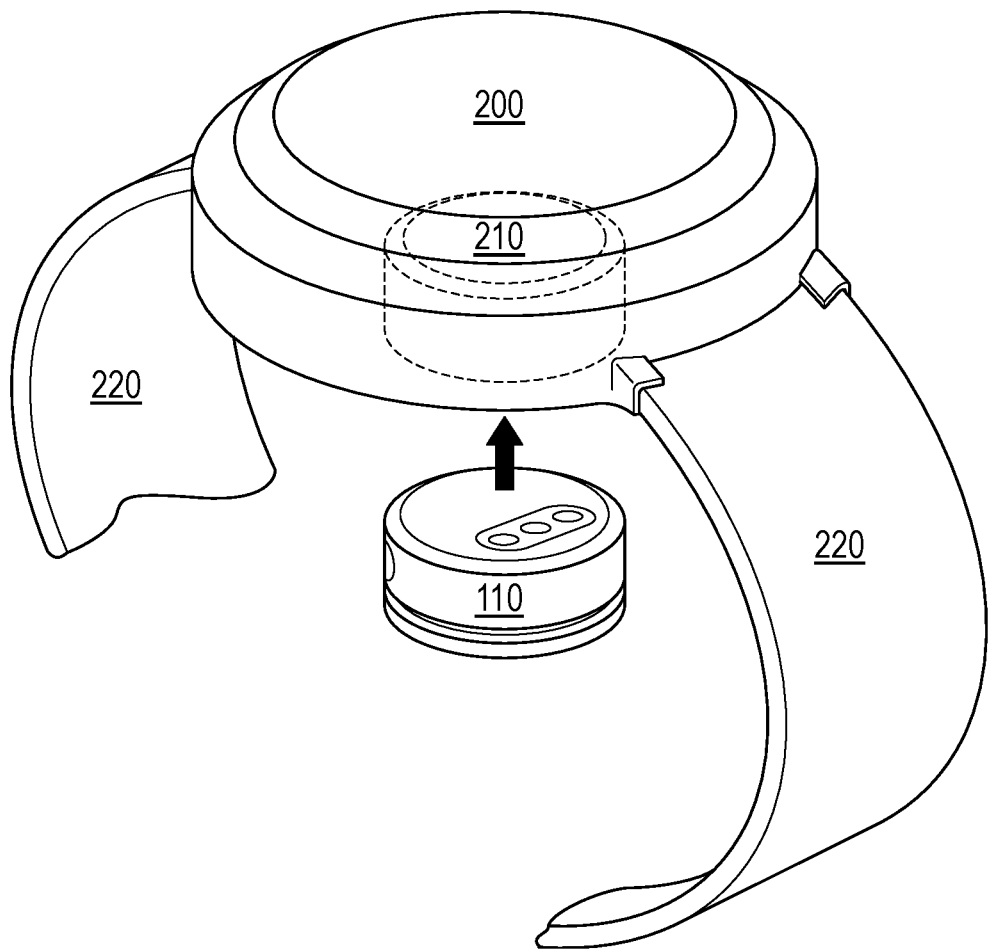
FIG. 16 is a perspective view of a thirteenth embodiment of the system.

In a first variation of this embodiment, the housing 110 fits within a cavity 210 defined by the wearable device 200 (e.g., as shown in FIG. 16). The sensor 130, electronics subsystem 150, and/or other system components are preferably operable to communicate with and/or receive power from (or send power to) the wearable device 200 (e.g., through an electrical connection, wirelessly, etc.), but can alternatively not communicate with and/or be powered by the wearable device 200. In examples of this variation, the fastener 140 can be operable to couple to the wearable device 200 by a latch (e.g., fastened by pressing the system 100 into the cavity 210 of the wearable device, unfastened by pressing a release button), a bayonet mount, a threaded barrel (e.g., wherein the fastener 140 includes threading around a cylindrical housing and is operable to screw into complementary threading on the cavity 210 of the wearable device), by one or more mechanical fasteners (e.g., screw, clip, etc.), can be retained by friction, adhesive, and/or van der Waals forces, and/or can be otherwise coupled or coupleable.

In a second variation of this embodiment, the fastener 140 attaches to a strap 220 or other fastening element of the wearable device 200 (e.g., as shown in FIGS. 14A-14E). For example, the housing 110 and fastener 140 can cooperatively encircle a strap 220 of the wearable device 200.

In a third embodiment, the fastener 140 attaches or is operable to attach the system 100 to a clothing article 12 (e.g., as shown in FIGS. 6A-6F, 7D, and 8A-8C). In this embodiment, the inlet 120 is retained on or proximal the skin surface 11 by the clothing article 12. In a first variation of this embodiment, the fastener 140 includes a clip operable to fasten near an edge of the clothing article 12 (e.g., to a waistband; bra strap, band, bridge, or cup; sock cuff; etc.). In a second variation, the housing 110 (e.g., a back side of the housing opposing the inlet 120) is attached to (e.g., adhered to, fused or sewn into, etc.) an interior surface of the clothing article 12.

In a fourth embodiment, the fastener 140 is operable to mount the system 100 directly to the user's skin (e.g., as shown in FIGS. 10A-10D). The fastener 140 preferably mounts the system 100 on, around, and/or near the skin surface 11 and preferably positions the inlet 120 on or near the skin surface 11. In variations of this embodiment, the fastener 140 can include an adhesive layer, a suction mount, a mount attachable by van der Waals forces, and/or any other suitable surface mount. However, the fastener 140 can include any other suitable mechanism for coupling the housing 110 to the user 10.

Figure 13:
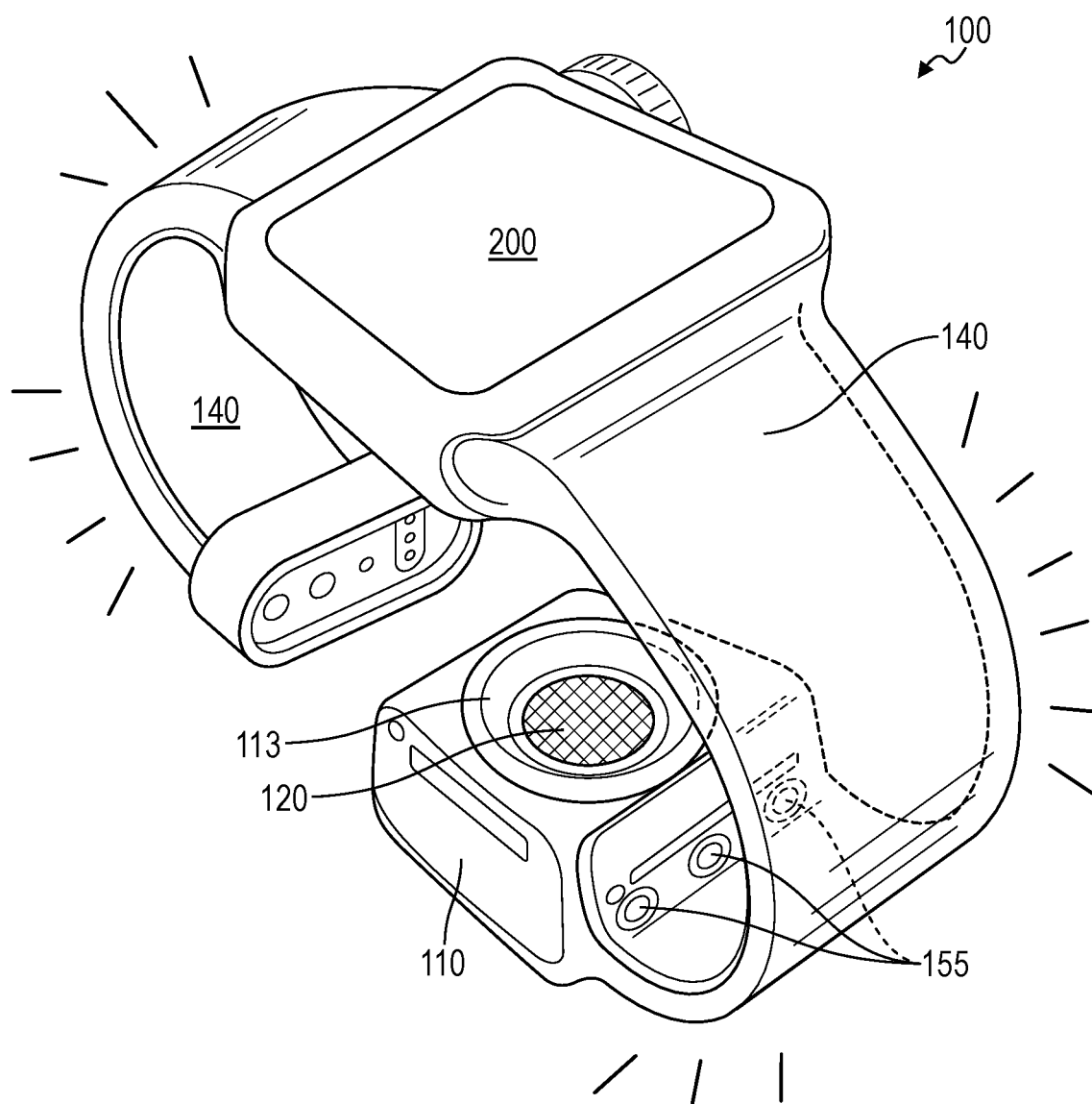
FIG. 13 is a perspective view of a tenth embodiment of the system.
Figure 14A:
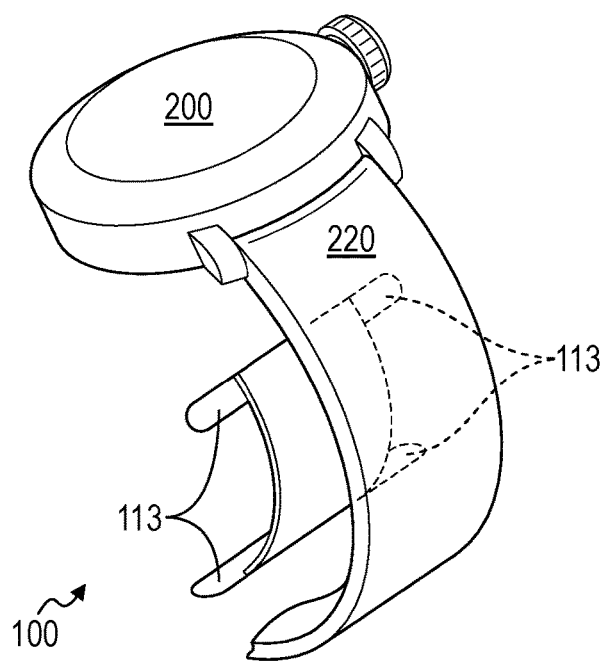
FIGS. 14A and 14B are perspective views of a first example of an eleventh embodiment of the system.
Figure 14B:
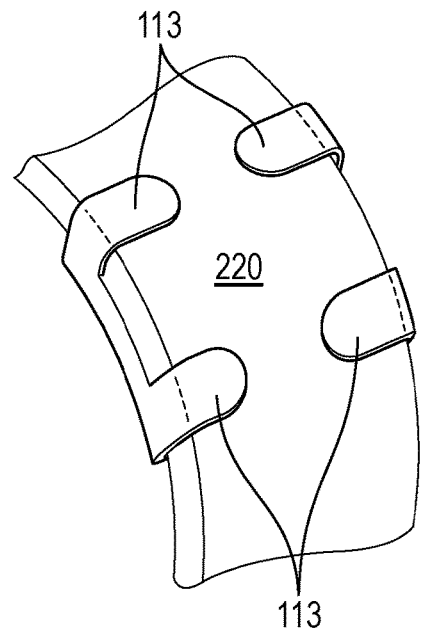
Figure 14C:
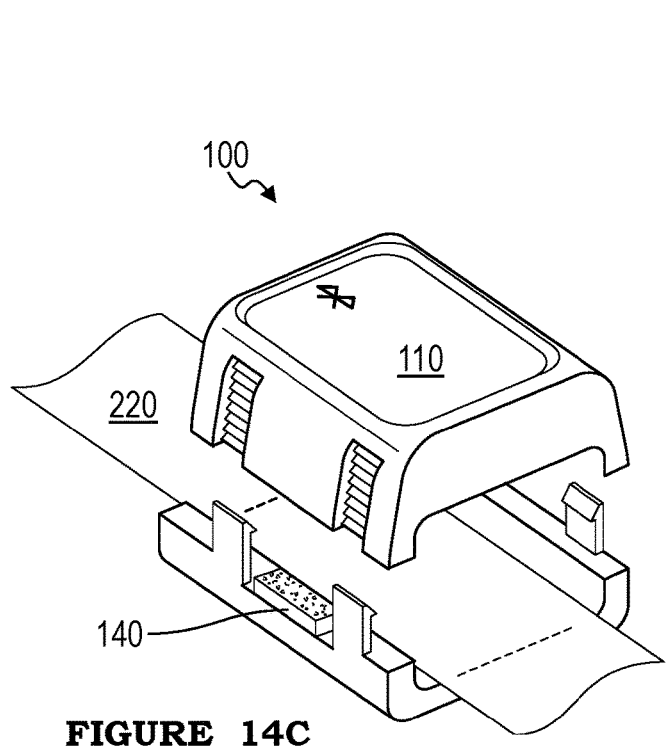
FIG. 14C is a perspective view of a second example of the eleventh embodiment.
Figure 14D:
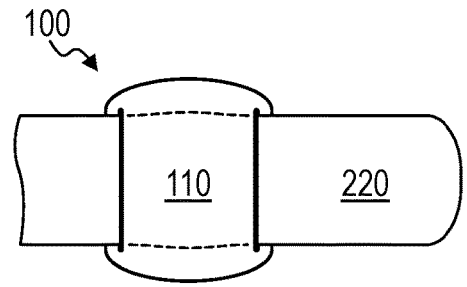
FIGS. 14D and 14E are a top view and a side view, respectively, of a third example of the eleventh embodiment.
Figure 14E:
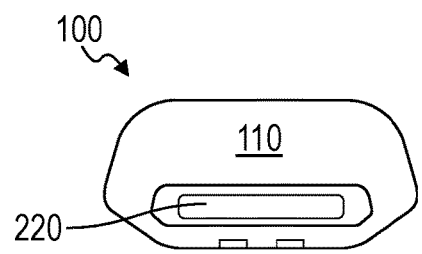

The fastener 140 (and/or housing 110) can include a display facilitating element that functions to allow a user to view information provided by one or more displays/light indicators of the system 100 (e.g., as shown in FIG. 13). For example, the fastener 140 and/or housing 110 can include a translucent region optically coupled to a light emitter (e.g., retained at or near a surface of the housing, such as near a connection between the fastener 140 and the housing 110)

and operable to conduct a light signal emitted by the light emitter. In a specific example, the light-emitting element is operable to emit light of several different colors, and a translucent region of a strap (e.g., a stripe along the strap, substantially the entire strap, etc.) glows in the color emitted by the light-emitting element. Such display facilitating elements can comprise elements and/or be configured in analogous ways to the elements described in one or more of: U.S. application Ser. No. 15/294,317, filed on 14 Oct. 2016 and U.S. application Ser. No. 14/470,376 filed 27 Aug. 2014, which are each incorporated in their entireties herein by this reference.

2.6 Calibration Element.

The system 100 can additionally or alternatively include one or more calibration elements. The calibration element can enable system self-calibration (e.g., by supplying a calibrated concentration of alcohol, by supplying a known quantity of alcohol, by supplying a quantity of alcohol with a specific time-release profile, etc.). The calibration element can be reusable or designed for a single calibration. In one embodiment, the calibration element is operable to cover the inlet 120 (e.g., by attaching to the housing 110). For example, the calibration element can be an adhesive patch, including a calibrated amount of alcohol, that can be applied to the backside of the housing 110 over the inlet 120 prior to use of the system 100 by a user. The system 100 can be worn with the calibration patch in place while the calibration process occurs, after which the calibration patch can be removed and the system 100 can be worn for normal use. In a second embodiment, the calibration element includes a chamber (e.g., sealed chamber) into which the system can be placed, and a calibrated alcohol environment can be maintained within the chamber.

The calibration element can additionally or alternatively include a temperature sensor configured to be in thermal communication with the user, by way of the housing and/or the fastener. The temperature sensor can function to enable temperature-based calibration of the sensor (e.g., adjusting sensor readings based on the measured temperature and a temperature calibration curve, such as a predetermined or dynamically determined calibration curve), and/or to detect when the system 100 is worn (e.g., wherein sustained increased temperature can indicate continuous wear, and temperature reduction can indicate removal of the system 100). However, the system 100 can include any suitable calibration elements and/or any other suitable elements.

3. Method.

Figure 17:
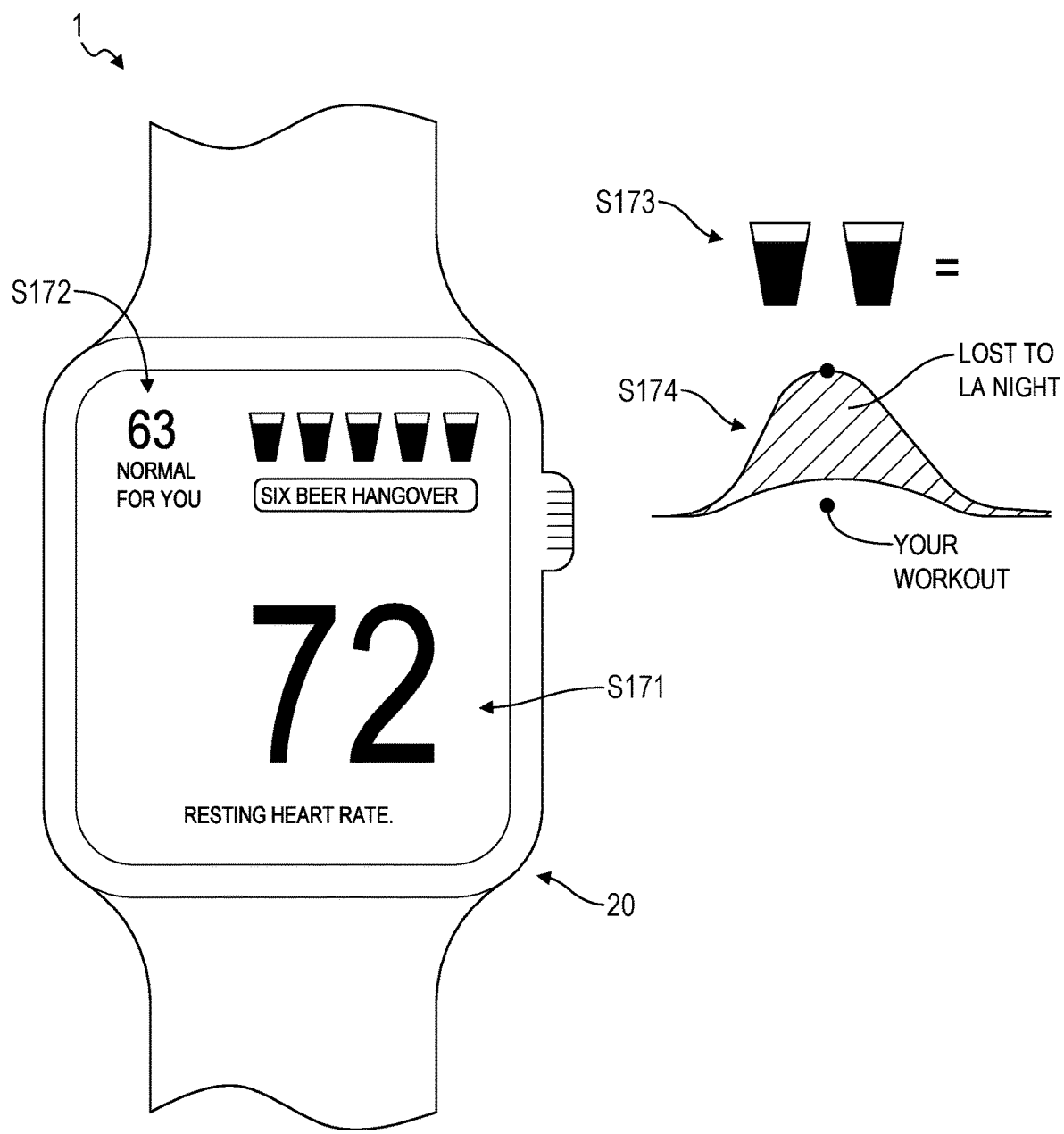
FIGS. 17-26 and 27A-27B are diagrams of various embodiments of the method.
Figure 18:
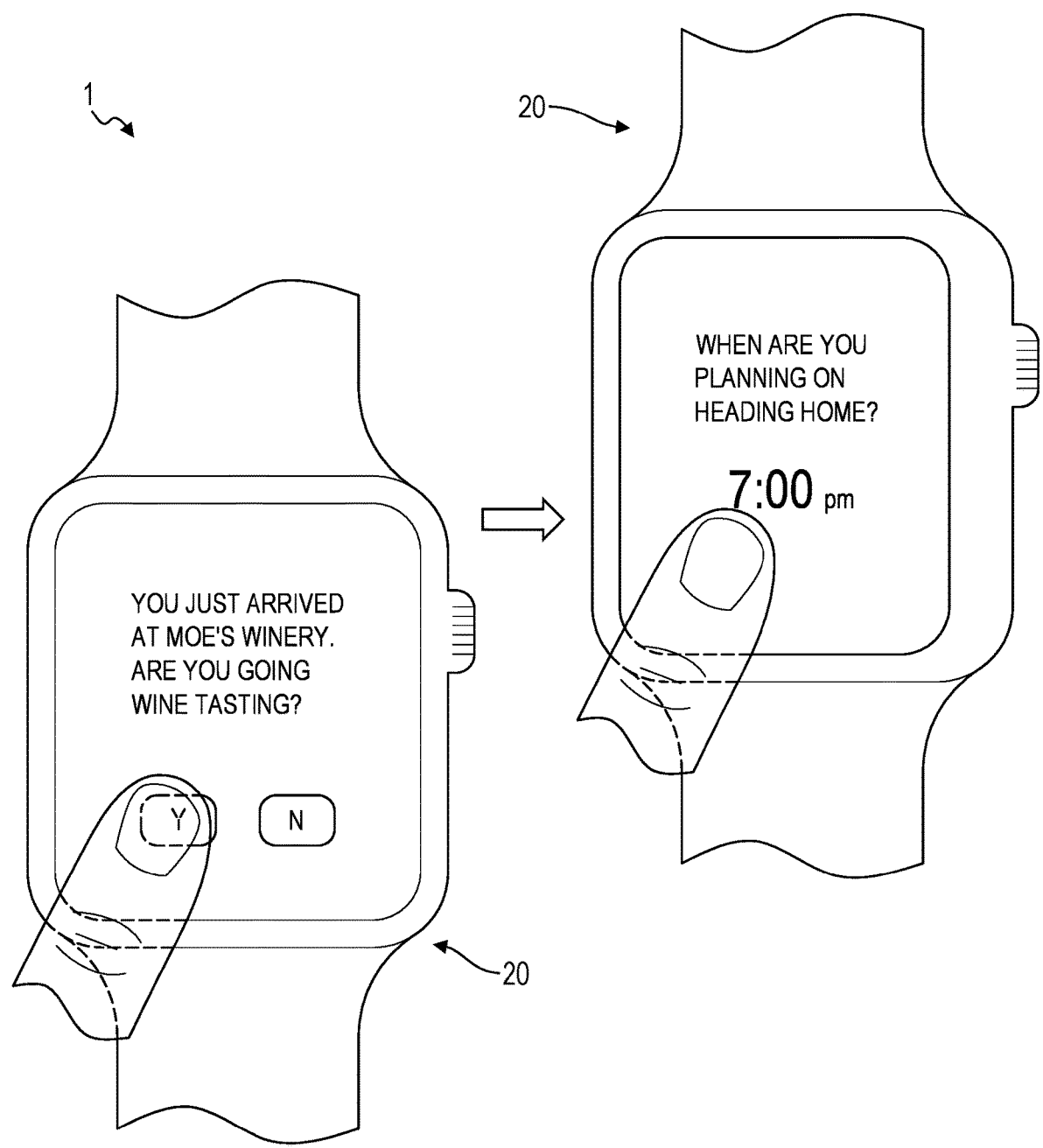
Figure 19:
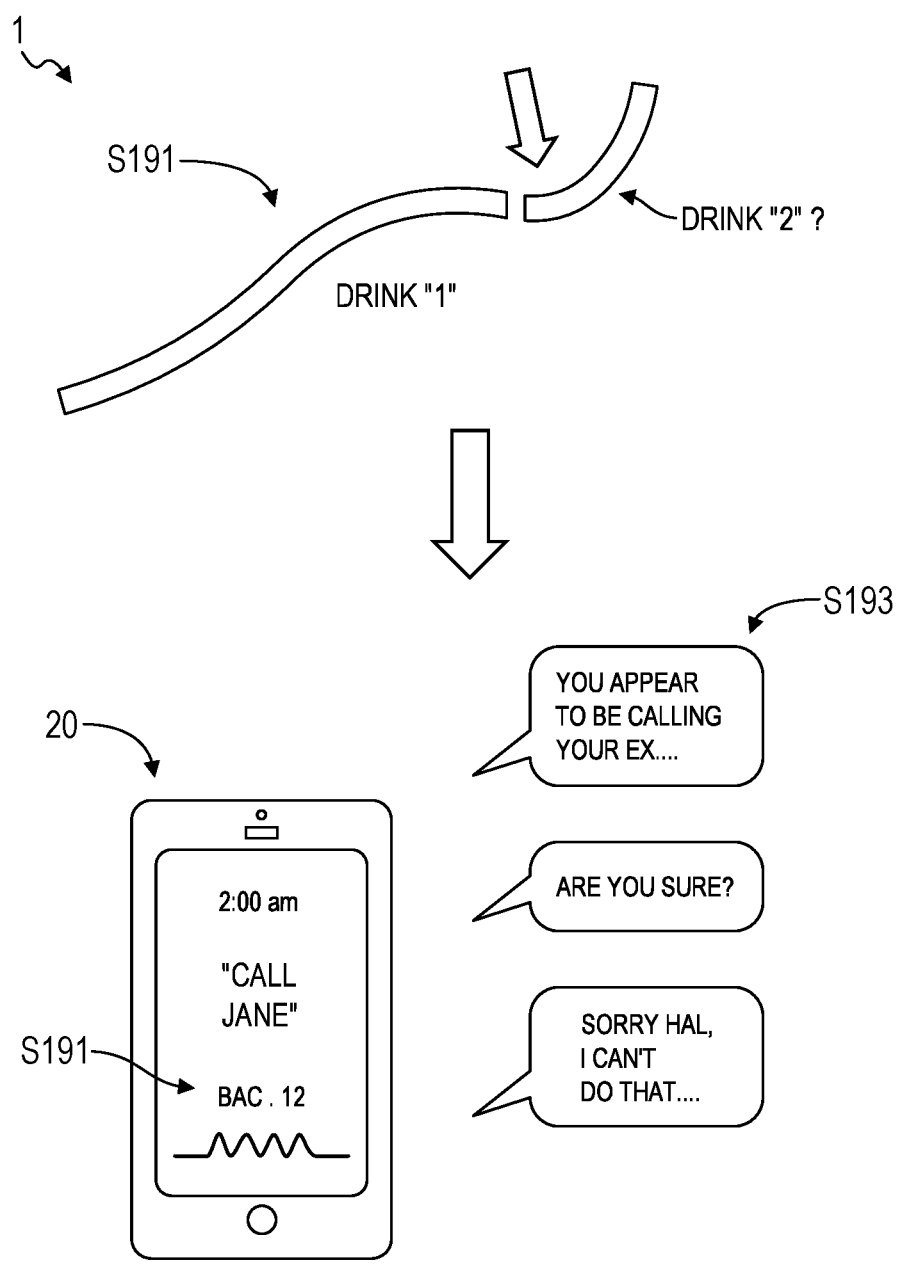
Figure 20:
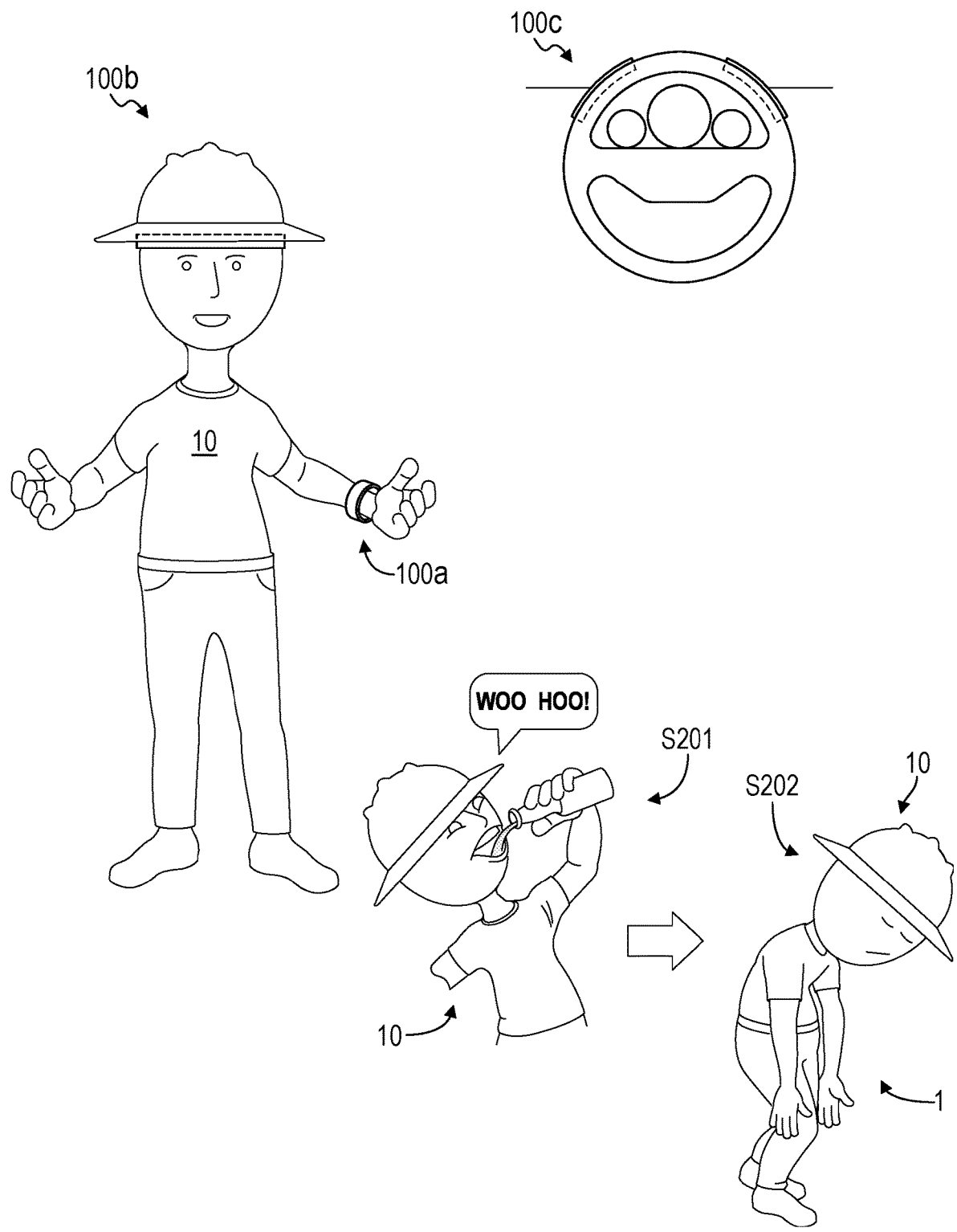
Figure 21:
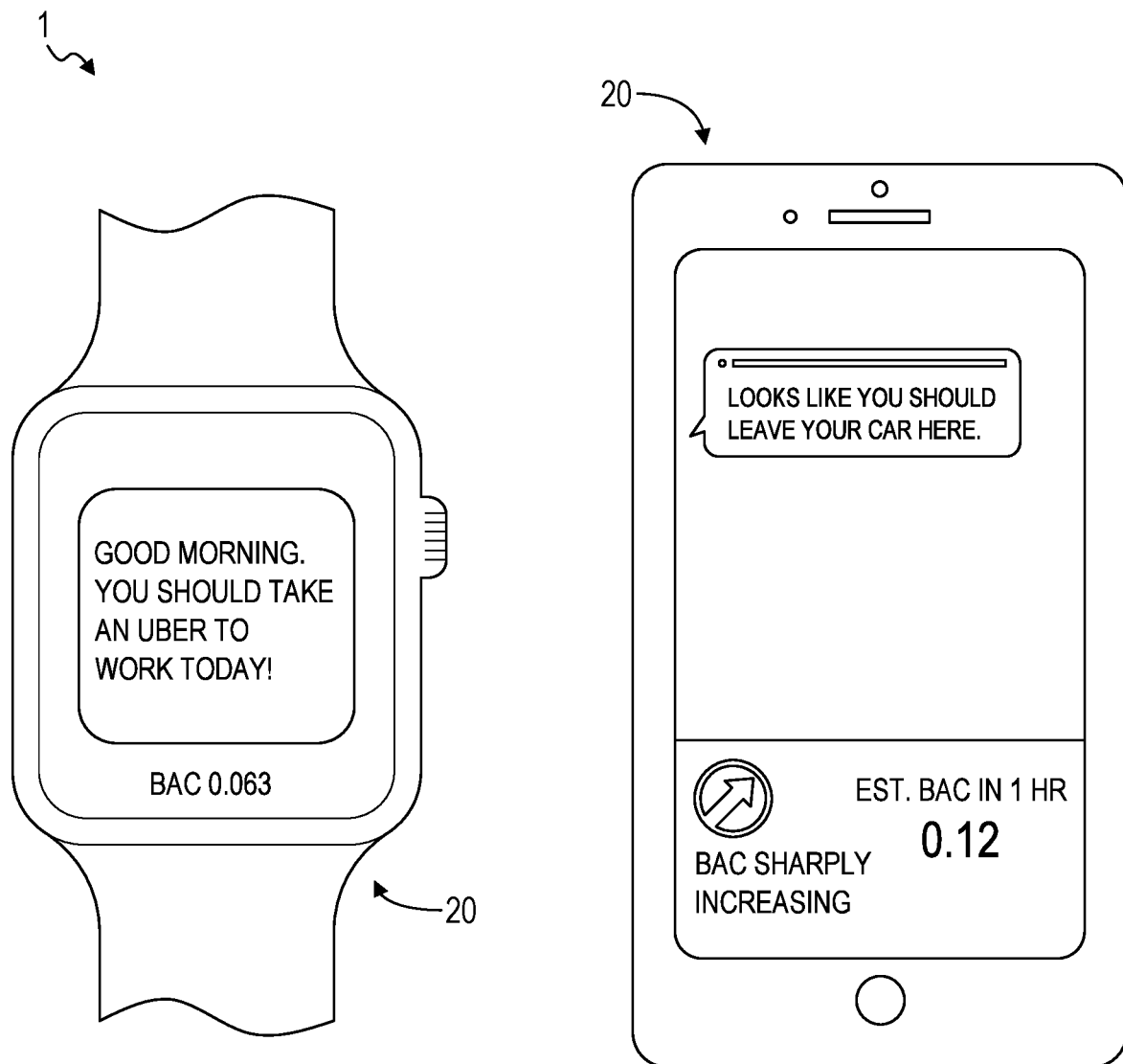
Figure 22:
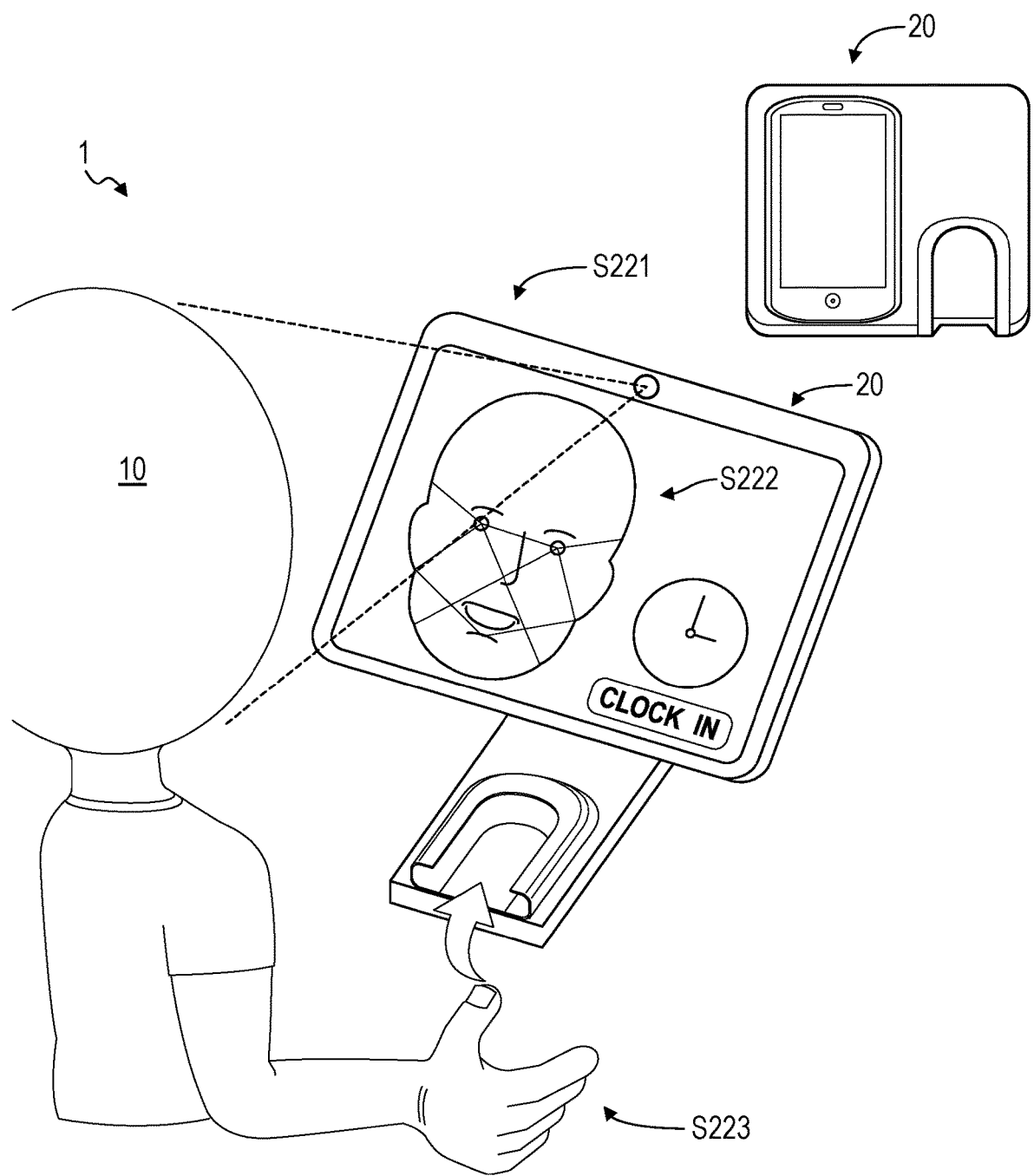
Figure 23:
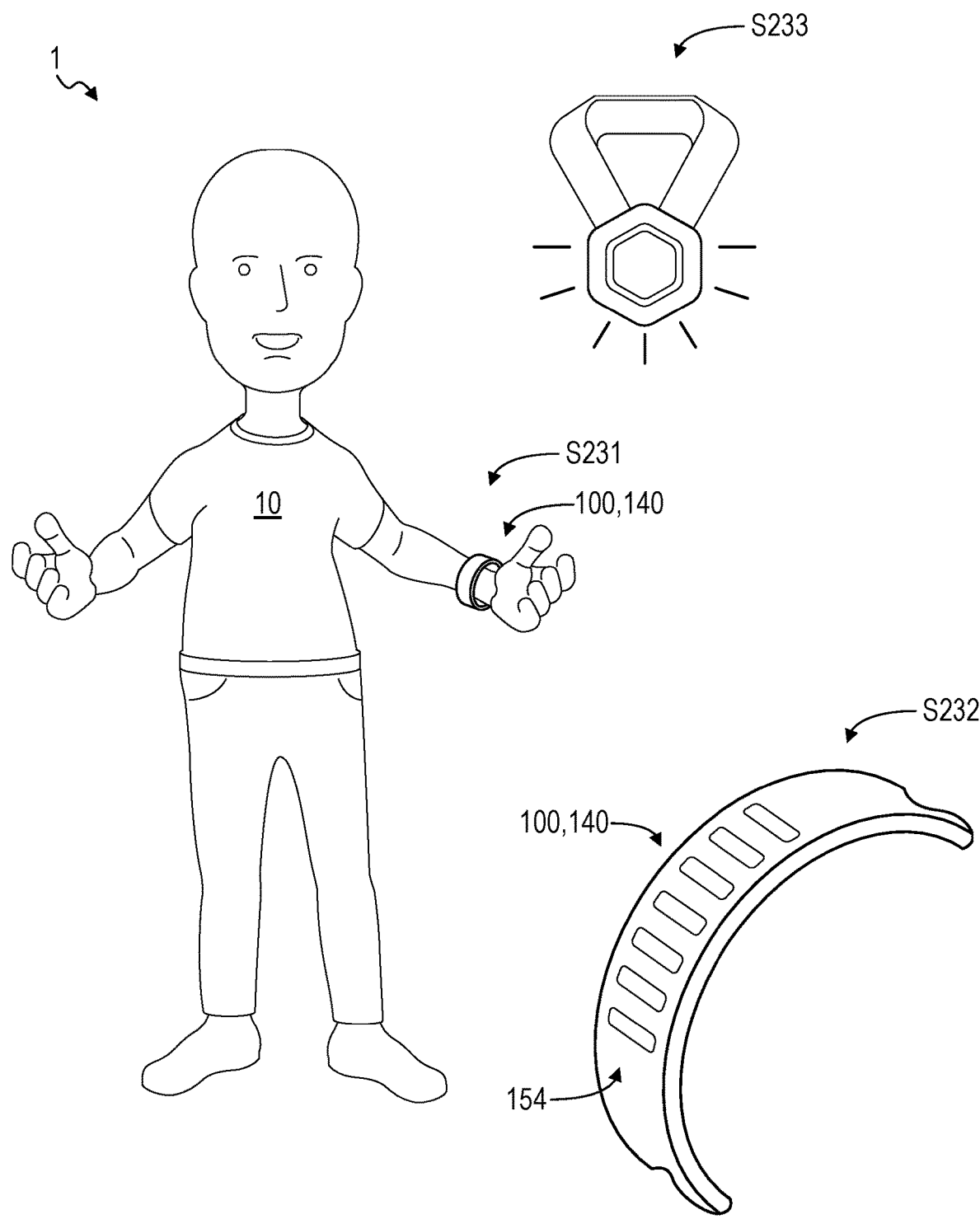
Figure 24:
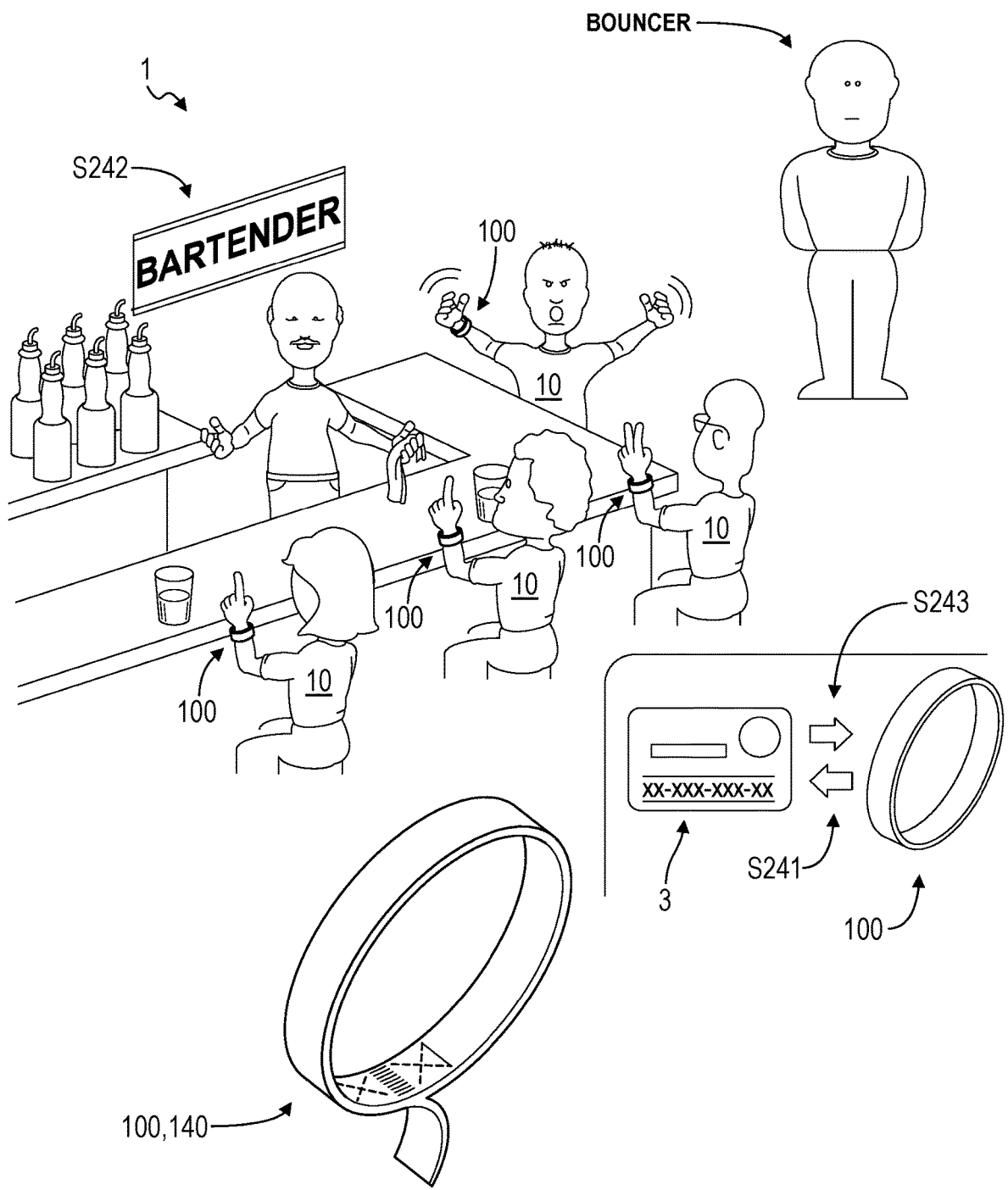
Figure 25:
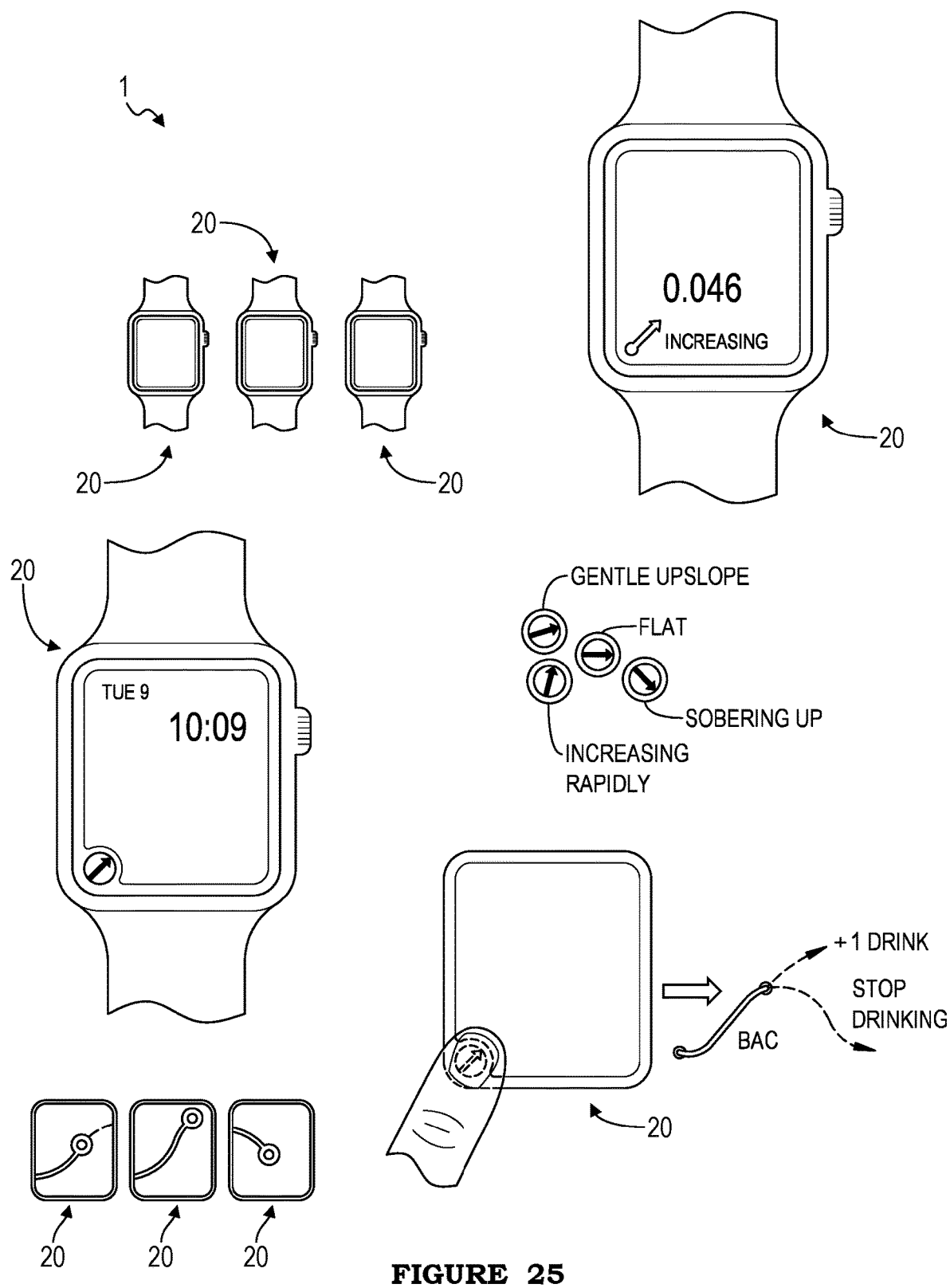
Figure 26:
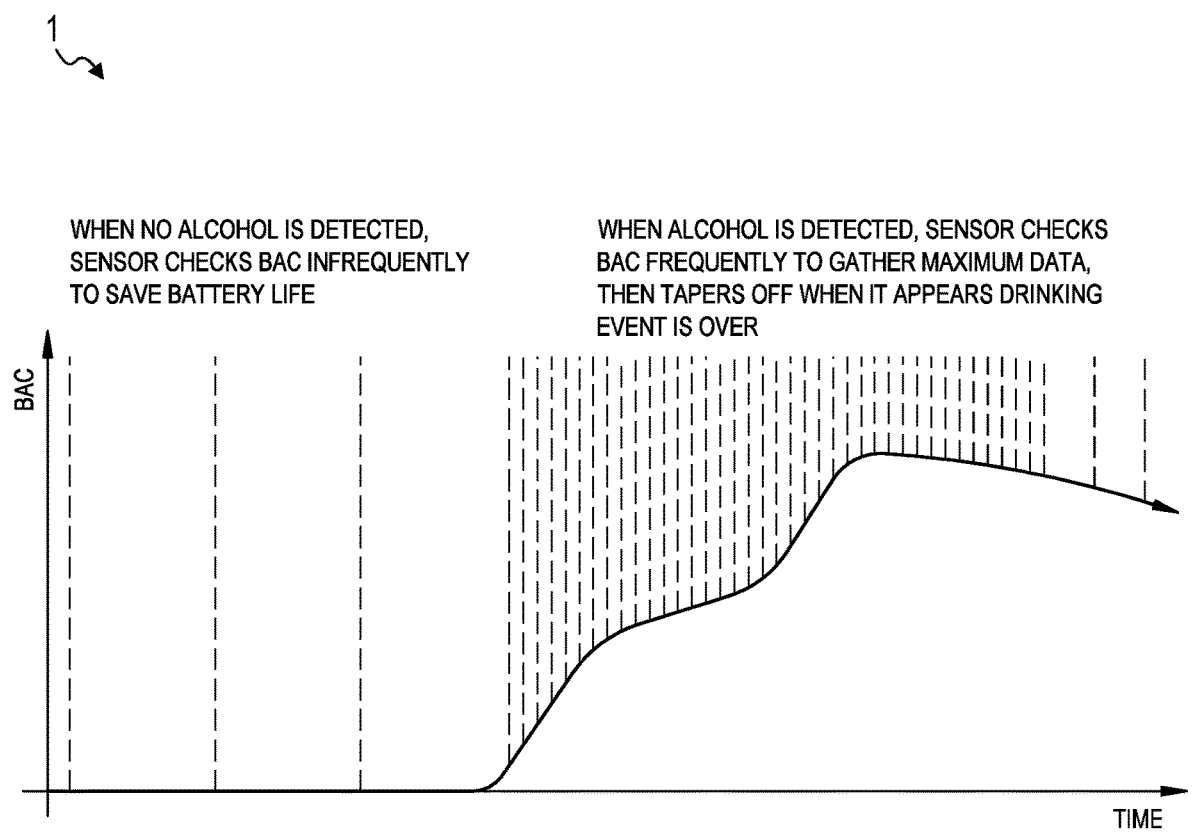

A method 1 for intoxication monitoring can be performed with a transdermal alcohol sensing system (e.g., the system 100 described above). In a first embodiment (e.g., as shown in FIG. 17), the method 1 can include determining correlations between alcohol consumption and other health metrics (e.g., sleep quality, weight, exercise, diet, heart rate, blood pressure, hangover symptoms, behavior characteristics, etc.) and presenting data about the other health metrics and/or the correlations to a user (e.g., at a user device, at the alcohol sensing system). In a second embodiment (e.g., as shown in FIG. 18), the method 1 can include determining that a user may consume more alcohol than safe or desired (e.g., at a winery tasting room, at a college party, etc.) and presenting recommendations to the user (e.g., stop drinking at a time that will allow the user to become sober before needing to drive, reduce the rate of drinking to avoid health risks, etc.). In a third embodiment (e.g., as shown in FIG. 19), the method 1 can include determining correlations between drinking events (e.g., sipping detected based on accelerometer data) and blood alcohol content and/or user performance on intoxication tests (e.g., puzzles, speech clarity, pupil dilation), presenting the correlations to the user, and/or preventing user actions (e.g., placing phone calls or sending text messages to predetermined contacts). In a fourth embodiment (e.g., as shown in FIGS. 20-22), the method 1 can include detecting user intoxication (e.g., through a worn alcohol sensor and/or an alcohol sensor integrated into a piece of equipment, such as a steering wheel of a vehicle or a sensor associated with an employee time logging system) and, in response to detecting intoxication, providing a warning (e.g., to the user, to a supervisor of the user, etc.) and/or preventing use of the equipment. In a fifth embodiment (e.g., as shown in FIG. 23), the method 1 can include presenting a visual indication of a user's ongoing sobriety (e.g., units of time such as days, weeks, or years since the user's last drinking event; awards associated with sobriety; etc.). In a sixth embodiment (e.g., as shown in FIG. 24), the method 1 can include presenting a visual indication of a user's current intoxication to another person (e.g., bartender) and/or preventing alcohol purchases by intoxicated users. In a seventh embodiment (e.g., as shown in FIG. 25), the method 1 can include determining a user's current, past, and/or projected intoxication and/or presenting an indication (e.g, visual indication, such as a numerical value, directed arrow, trendline, etc.) of the intoxication (e.g., to the user, at a wearable electronic device, etc.). In some embodiments, the method 1 can include (e.g., as shown in FIG. 26) controlling the sensor to collect data less frequently when frequent readings are not desired (e.g., when no alcohol is detected) and/or controlling the sensor the sensor to collect data more frequently (e.g., at a maximum sampling rate) when frequent readings are desired (e.g., when alcohol is detected), which can function to reduce power consumption.

Figure 27A:
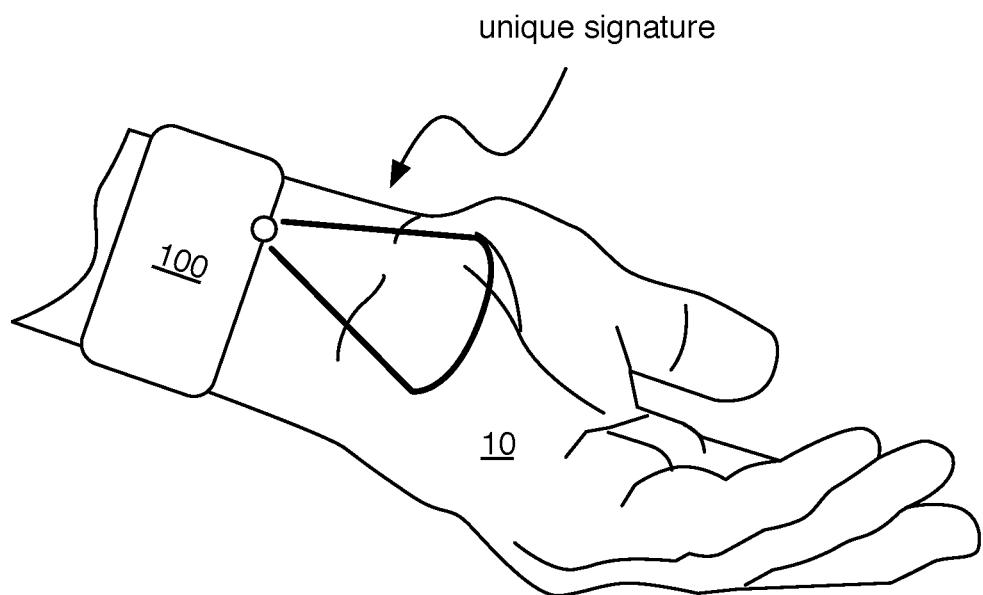
Figure 27B:
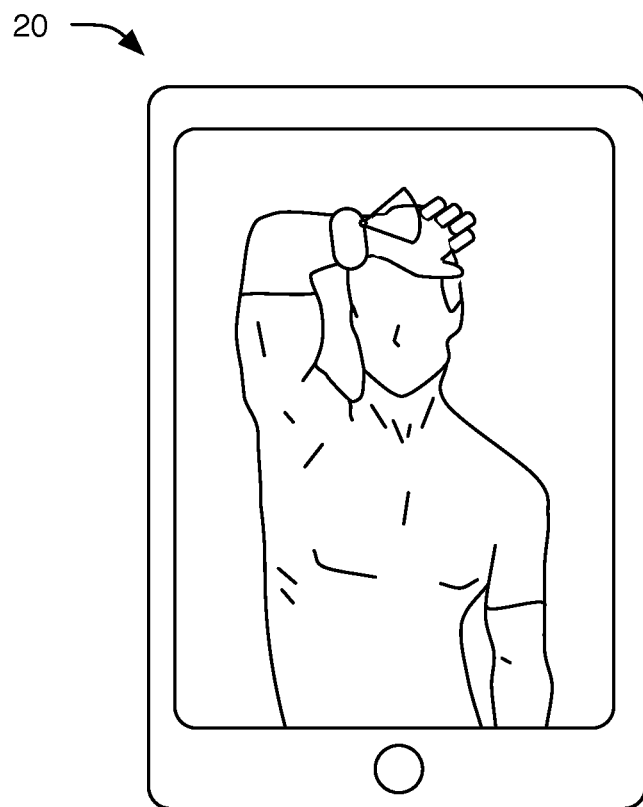
Figure 28A:
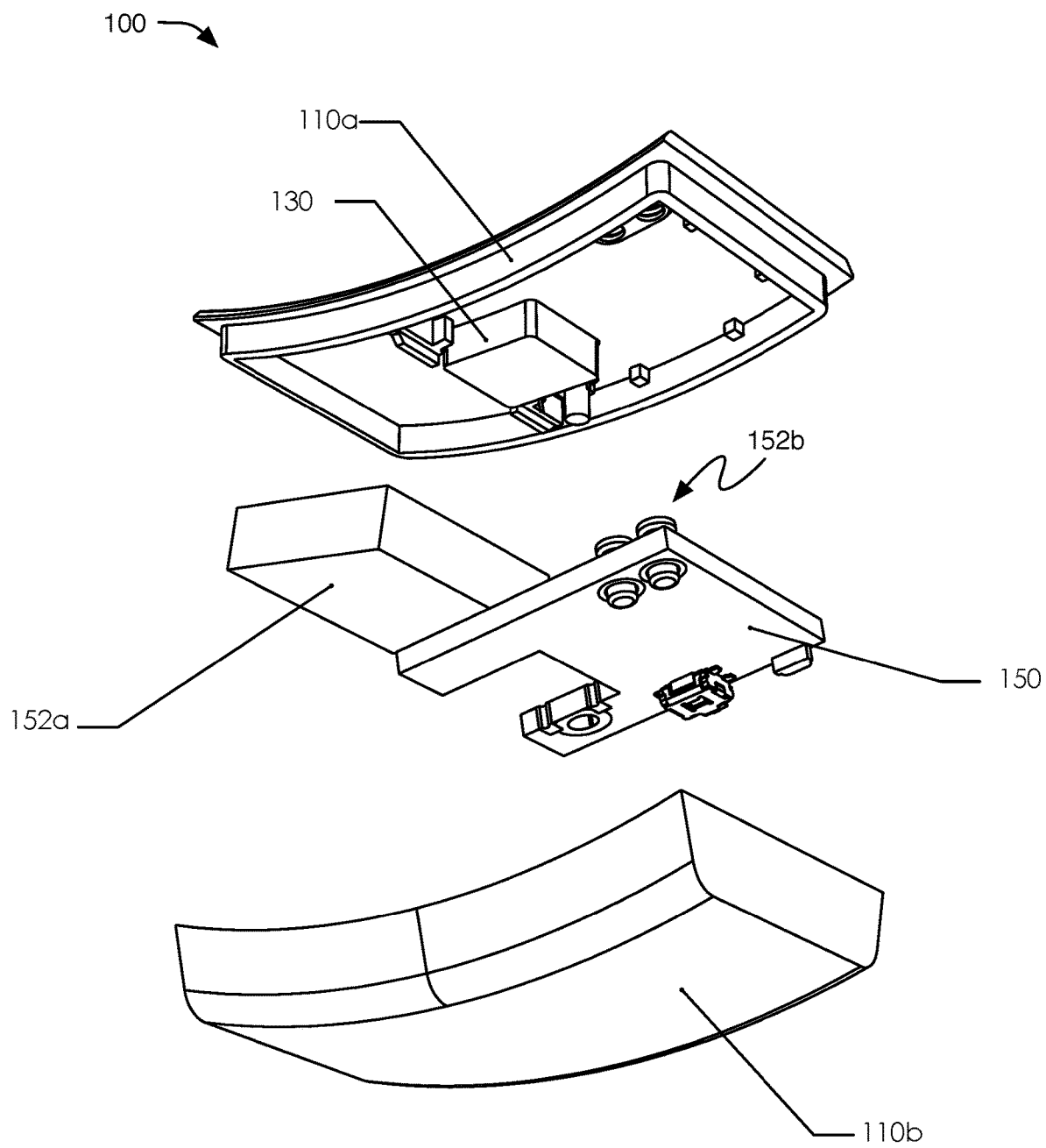
FIGS. 28A-28C are a first exploded view, a second exploded view, and a cross-sectional view of a first example of a fourteenth embodiment of the system.
Figure 28B:
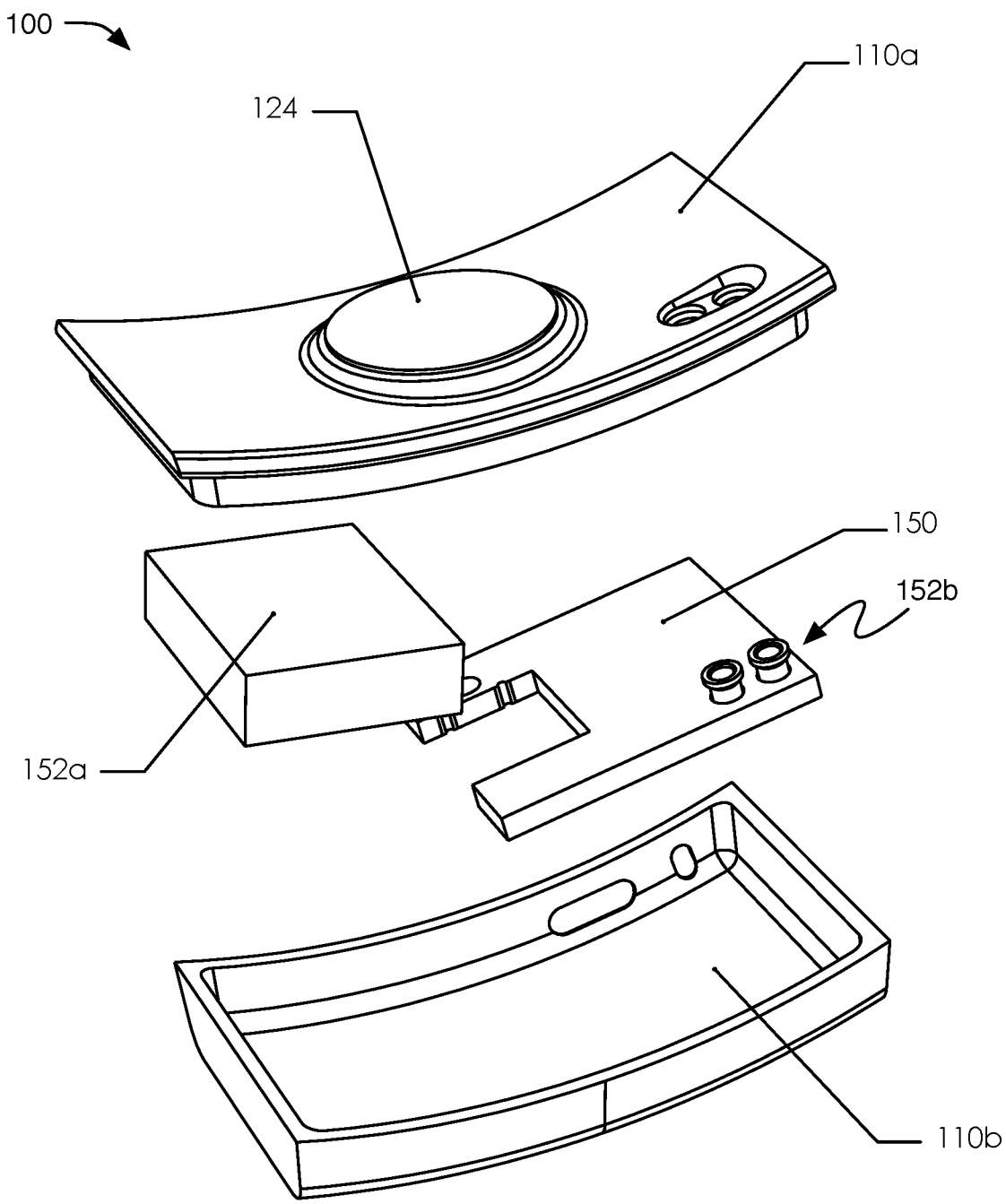
Figure 28C:
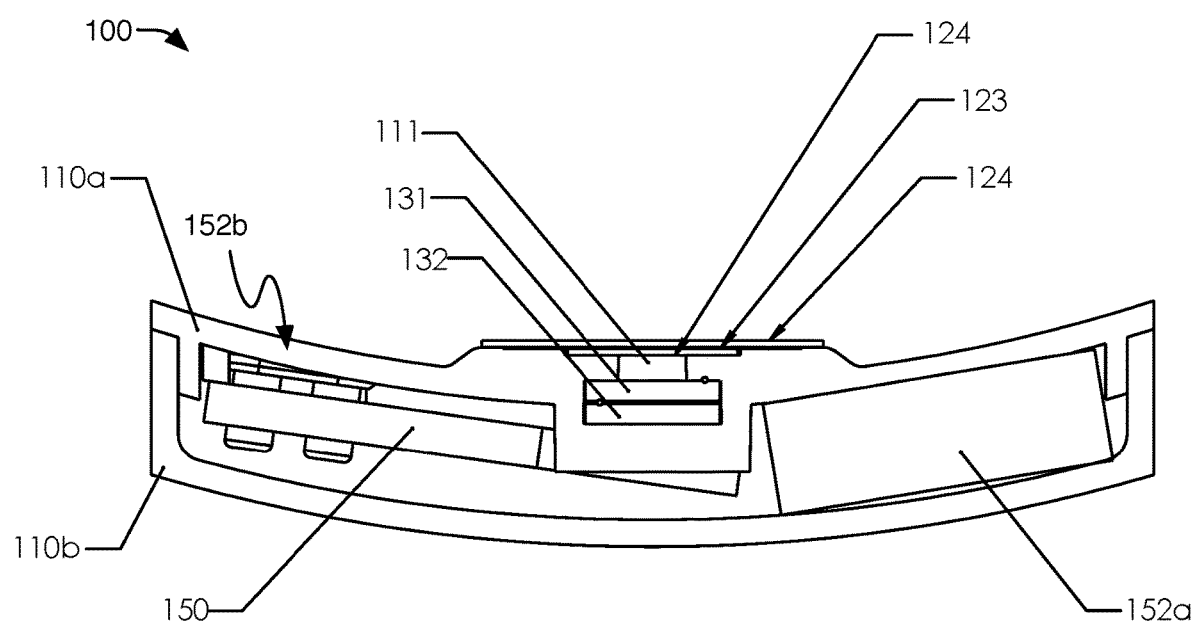
Figure 29A:
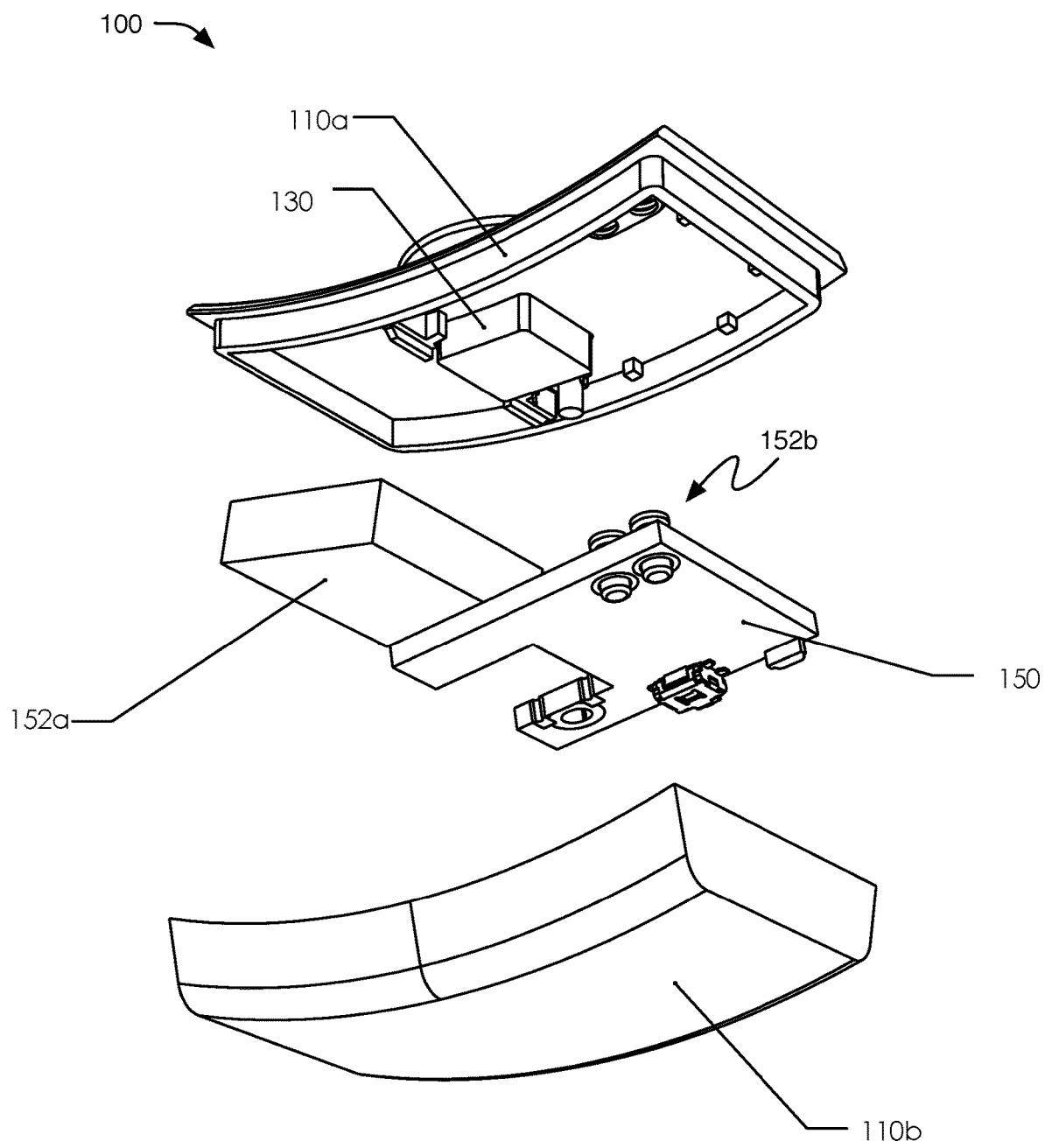
FIGS. 29A-29C are a first exploded view, a second exploded view, and a cross-sectional view of a second example of a fourteenth embodiment of the system.
Figure 29B:
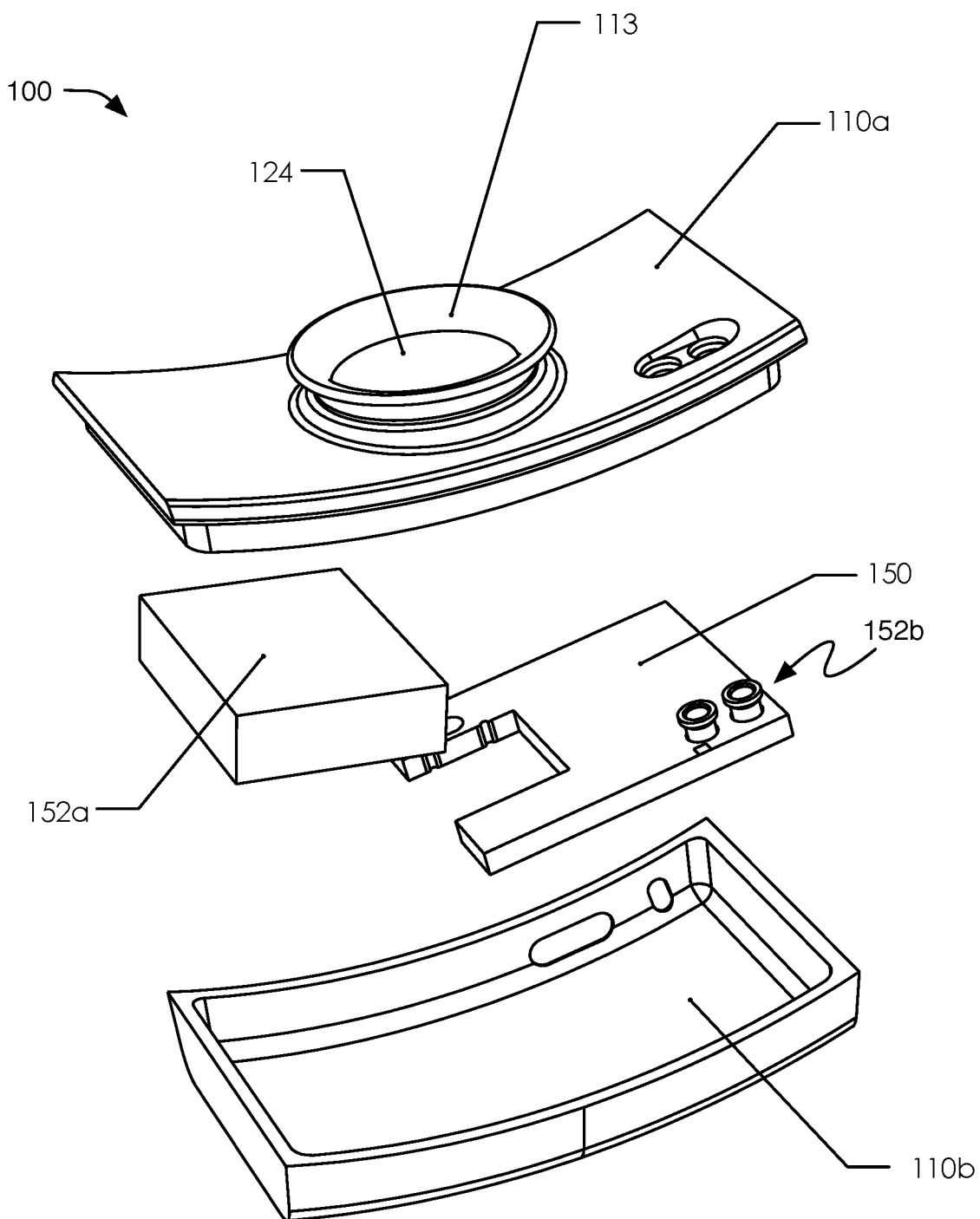
Figure 29C:
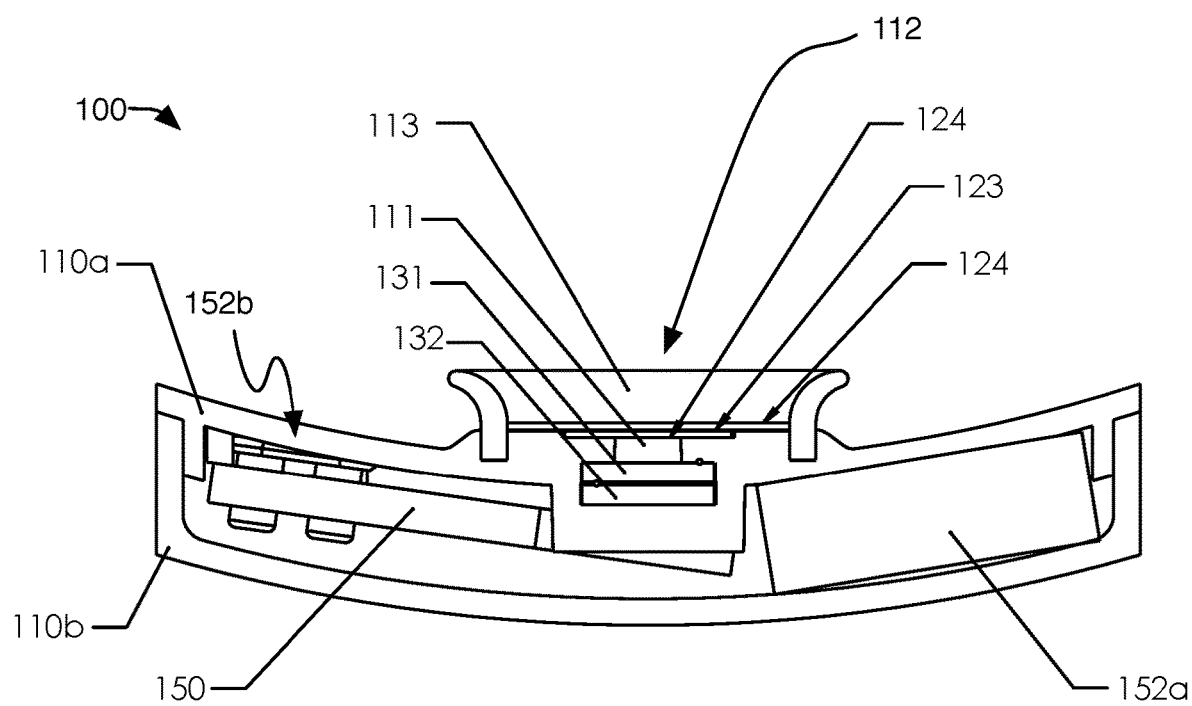

However, the method 1 can include any other suitable blocks or steps, some embodiments, variations, and examples of which are described in U.S. application Ser. No. 15/294,317 filed on 14 Oct. 2016, U.S. application Ser. No. 14/470,376 filed 27 Aug. 2014, U.S. application Ser. No. 14/602,919, and U.S. application Ser. No. 15/205,876, which are each incorporated herein in their entireties by this reference. For example, the system 100 can include an output (e.g., optical output, such as a light emitter or electronic display; audio output; etc.) operable to output a unique signature, and the method 1 can include acquiring sensor data including a photograph or video displaying the user 10 wearing the system 100 and including the unique signature (e.g., in the photograph or video), examples of which are shown in FIGS. 27A-27B.

The preferred embodiments include every combination and permutation of the various system components and the various method processes. Furthermore, various processes of the preferred method can be embodied and/or implemented at least in part as a machine configured to receive a computer-readable medium storing computer-readable instructions. The instructions are preferably executed by computer-executable components preferably integrated with the system and one or more portions of the electronics subsystem 150. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processing subsystem, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for transdermal alcohol sensing, the system comprising:
    an alcohol sensing device configured to be worn by a user and interface with an alcohol sensor, the alcohol sensing device comprising:
        a housing coupled to the alcohol sensor;
        a power source coupled to the housing and electrically coupled to the alcohol sensor by way of the housing; and
        a fastener coupled to the housing and operable to position the alcohol sensor proximal to a skin surface of the user;
    a processing system communicatively coupled to the alcohol sensing device, wherein the processing system is operable to receive a time series of signals from the alcohol sensor and continuously determine a time series of blood alcohol content (BAC) metrics based on the time series of signals; and
    an electronic display coupled to the processing system, wherein the processing system is operable to control the electronic display based on the time series of BAC metrics, and wherein the electronic display displays an estimated time point at which the user will reach a state of sobriety, wherein the estimated time point is determined at the processing system based on the time series of BAC metrics.

2. The system of claim 1, wherein the alcohol sensing device further comprises an electronics subsystem mounted to the housing, wherein the electronics subsystem is configured to receive the time series of signals from the alcohol sensor and transmit the time series of signals to the processing system.

3. The system of claim 2, wherein the processing system further comprises an application configured to execute on a mobile device, the mobile device comprising the electronic display and separate from the alcohol sensing device.

4. The system of claim 1, wherein the electronic display further displays a predicted temporal profile of the BAC metric for the user over time.

5. The system of claim 1, wherein the processing system comprises a first processing subsystem located at the alcohol sensing device and a second processing subsystem remotely located from the alcohol sensing device, wherein the system further comprises a data link between the first and second processing subsystems, wherein in the event that the BAC metric exceeds a predetermined threshold, the second processing subsystem transmits a notification to the first processing subsystem via the data link.

6. The system of claim 5, wherein the housing further comprises an indicator element, wherein the notification triggers the indicator element to transition from an "off" to an "on" state.

7. The system of claim 6, wherein the indicator element comprises a vibration motor.

8. A system for transdermal alcohol sensing, the system comprising:
    an alcohol sensor;
    a housing coupled to the alcohol sensor;
    a processing system operable to receive signals from the alcohol sensor, wherein a first processing subsystem of the processing system is coupled to an electronic display, wherein the first processing subsystem is operable to determine a value of a blood alcohol content (BAC) metric based on the signals, and wherein the electronic display comprises an estimated time point at which the user will reach a state of sobriety based on the value of the BAC metric;
    a light emitter connected to the housing, wherein the processing system is operable to control an operation mode of the light emitter;
    a vibration motor connected to the housing, wherein the processing system is operable to control an operation mode of the vibration motor; and
    a fastener coupled to the housing and operable to position the alcohol sensor proximal to a skin surface of the user.

9. The system of claim 8, wherein the first processing subsystem is further operable to control the electronic display based on the value of the BAC metric.

10. The system of claim 9, wherein the first processing subsystem is located remotely from the housing.

11. The system of claim 8, wherein the electronic display further comprises a predicted temporal profile of the BAC metric for the user over time.

12. The system of claim 8, wherein the processing system further comprises a second processing subsystem, separate from the first processing subsystem, the second processing subsystem mounted to the housing, wherein the second processing subsystem is configured to receive a notification from the first processing subsystem, the notification comprising a determination from the first processing subsystem that the BAC metric has exceeded a predetermined threshold, wherein the second processing subsystem is configured to trigger a transition in operation mode of at least one of the light emitter and vibration motor in response to notification receipt.

13. The system of claim 12, wherein the transition in operation mode comprises a transition from an "off" state to an "on" state of the vibration motor.

14. The system of claim 8, wherein the fastener comprises a flexible polymer, the flexible polymer operable to retain the alcohol sensor against the skin surface of the user.

15. The system of claim 8, wherein the alcohol sensor comprises a microporous membrane permeable to ethanol vapor and substantially impermeable to water.

16. The system of claim 8, further comprising an electrical jack electrically coupled to the alcohol sensor, the electrical jack operable to receive an electrical power input.

17. The system of claim 8, wherein the alcohol sensor comprises a fuel cell.

18. A system for transdermal alcohol sensing, the system comprising:
- an alcohol sensor;
- a housing coupled to the alcohol sensor;
- a processing system operable to receive signals from the alcohol sensor, wherein a first processing subsystem of the processing system is coupled to an electronic display and located remotely from the housing, wherein the first processing subsystem is operable to:
  - determine a value of a blood alcohol content (BAC) metric based on the signals; and
  - control the electronic display based on the value of the BAC metric;
- a light emitter connected to the housing, wherein the processing system is operable to control an operation mode of the light emitter;
- a vibration motor connected to the housing, wherein the processing system is operable to control an operation mode of the vibration motor; and
- a fastener coupled to the housing and operable to position the alcohol sensor proximal to a skin surface of the user.

* * * * *